(12) United States Patent
van den Heuvel

(10) Patent No.: US 12,145,001 B2
(45) Date of Patent: Nov. 19, 2024

(54) TREATMENT PLANNING SYSTEM

(71) Applicant: Frank van den Heuvel, Berchem (BE)

(72) Inventor: Frank van den Heuvel, Berchem (BE)

( * ) Notice: Subject to any disclaimer, the term of this patent is extended or adjusted under 35 U.S.C. 154(b) by 199 days.

(21) Appl. No.: 18/011,323

(22) PCT Filed: Jun. 28, 2021

(86) PCT No.: PCT/GB2021/051629
§ 371 (c)(1),
(2) Date: Dec. 19, 2022

(87) PCT Pub. No.: WO2021/260395
PCT Pub. Date: Dec. 30, 2021

(65) Prior Publication Data
US 2024/0009483 A1    Jan. 11, 2024

(30) Foreign Application Priority Data

Jun. 26, 2020 (GB) ..................................... 2009822
Nov. 24, 2020 (GB) ..................................... 2018474

(51) Int. Cl.
*A61N 5/10*    (2006.01)
*G16H 20/40*   (2018.01)

(52) U.S. Cl.
CPC ........... *A61N 5/103* (2013.01); *A61N 5/1064* (2013.01); *G16H 20/40* (2018.01)

(58) Field of Classification Search
None
See application file for complete search history.

(56) References Cited

U.S. PATENT DOCUMENTS

2021/0330913 A1* 10/2021 Martin .............. A61M 16/0069
2022/0237999 A1*  7/2022 Shelton, IV ......... A61B 5/7267
(Continued)

FOREIGN PATENT DOCUMENTS

WO    2020018904 A1    1/2020
WO    2020185544 A1    9/2020

OTHER PUBLICATIONS

Effect of high dose rates on survival of mammalian cells by Town, C. D. in Nature 215, 847-848, DOI:10.1038/215847a0 (1967).
(Continued)

*Primary Examiner* — Hoon K Song
(74) *Attorney, Agent, or Firm* — Downs Rachlin Martin PLLC

(57) ABSTRACT

We describe a method and a computer system for analysing a radiation treatment plan using a dose of flash radiation to irradiate a volume within a patient and a radiation treatment system using the same. The computer system comprises a processor which is configured to obtain oxygen pressure information for the volume to be irradiated; obtain parameters from a patient treatment plan; input the obtained oxygen pressure information and parameters in to a model which predicts complex damage within the irradiated volume caused by the dose of flash radiation; output a prediction, using the model, of the complex damage caused within the volume by the dose of flash radiation; and quantify, using the prediction, a level of damage to healthy tissue within the irradiated volume. Complex damage is damage which is more complex than a double strand break within DNA in patient tissue and the model is a function of energy of particles within the radiation and oxygen pressure which varies with time.

23 Claims, 16 Drawing Sheets

(56) References Cited

U.S. PATENT DOCUMENTS

| | | | | |
|---|---|---|---|---|
| 2023/0125147 A1* | 4/2023 | Khuntia | ................ | A61N 5/103 378/65 |
| 2023/0270960 A1* | 8/2023 | Acker | ................... | G16H 20/13 128/203.14 |

OTHER PUBLICATIONS

"Irradiation in a flash: Unique sparing of memory in mice after wholebrain irradiation with dose rates above 100Gy/s" by Montay-Gruel, P.et al in Radiother. Oncol. 124, 365-369, DOI: https://doi.org/10.1016/j.radonc.2017.05.003 (2017).

Oxygen tension distributions are sufficient to explain the local response of human breast tumors treated with radiation alone by Okunieff et al published in the International Journal of Radiation 1993, 26(4): 631-636.

Effects of radiation quality and oxygen on clustered DNA lesions and cell death by Stewart et al published in Radiation research in 2011; 176(5):587-602.

"An experimental and analytical study of oxygen depletion in stirred cell suspensions" by Whillans et al published in Radiation Research 84, 97-114 (1980).

"Time scale of radiation-induced oxygen depletion and decay kinetics of oxygen-dependent damage in cells irradiated at ultrahigh dose rates" by Ling published in 1975 in Radiat. Research 63, 455-67.

"The physical basis of IMRT and inverse planning" by S Webb The British Journal of Radiology 2003 76:910, 678-689.

Multiple local minima in radiotherapy optimization problems with dose-volume constraints by Deasy et al published in Med.Phys. 241157-61 [From Spec—need copy].

"Sequential annealing-gradient gamma-knife radiosurgery optimization" by Ove et al published in Phys. Medicine Biol.48, 2071-2080, 2003.

Dynamic string-averaging cq-methods for the split feasibility problem with percentage violation constraints arising in radiation therapy treatment planning by Brooke et al published in 2019.

"Saturation behaviour: a general relationship described by a simple second-order differential equation" by Kepner et al published in Theoretical biology and medical modelling 2010; 7:11-11.

"A mechanistic investigation of the oxygen fixation hypothesis and oxygen enhancement ratio" by Grimes et al published in Biomedical physics and engineering express 2015.

A closed parametrization of DNA-damage by charged particles, as a function of energy—a geometrical approach by Van den Heuvel et al published in PLoS One 2014.

"Significance testing of the spearman rank correlation coefficient" by Zar et al published in J. Am. Stat. Assoc. 67, 578-580 in 1972 [From Spec—need copy].

"Implementation of a new optimization algorithm in VMAT for the treatment of prostate cancer" by Birba et al published in Physica Medica, vol. 44, Supplement 1,201 pp. 38-39, 2017.

PCT International Search Report and Written Opinion dated Oct. 1, 2021, in International Application No. PCT/GB2021/051629.

Guillem Pratx et al., "A computational model of radiolytic oxygen depletion during FLASH irradiation and its effect on the oxygen enhancement ratio." Department of Radiation Oncology, Standford University School of Medicine (May 16, 2019).

UK Intellectual Property Search Report issued in priority Application No. GB2009822.4 on Dec. 11, 2020.

* cited by examiner

TREATMENT PLANNING SYSTEM

FIELD

The invention relates to a radiation treatment planning system, particularly a high dose rate radiation treatment such as flash radiotherapy.

BACKGROUND

Radiation therapy is well known, for example in treating cancer. Radiation therapy involves directing a beam of high energy proton, photon, ion or electron radiation into a target (e.g. a tumour). It is desirable to have a tissue sparing radiotherapy in which the radiotherapy minimises the damage to the healthy tissue surrounding the target. A more recently developed radiation therapy is known as flash radiotherapy and this involves the ultra-fast delivery of radiation treatment at dose rates which are several orders of magnitude greater than those currently in routine clinical practice. For example, the dose may be delivered using pulsed radiation at rates which are of the order of 40 Gy/s. A number of groups have shown that in these conditions a tissue sparing effect can occur with the therapy having a reduced effect on normal biological tissue but a constant effect on tumour. This beneficial effect of flash radiotherapy may be termed a flash effect. Examples illustrating the effect include "Effect of high dose rates on survival of mammalian cells" by TOWN, C. D. in Nature 215, 847-848, DOI: 10.1038/215847a0 (1967) or "Irradiation in a flash: Unique sparing of memory in mice after wholebrain irradiation with dose rates above 100 Gy/s" by Montay-Gruel, P. et al in Radiother. Oncol. 124, 365-369, DOI: https://doi.org/10.1016/j.radonc.2017.05.003 (2017).

The presence of oxygen during irradiation of living tissue is known to have an important dose-enhancing property, particularly when delivering radiation using a low linear energy transfer (LET) modality such as photons, electrons and protons. In clinical practice, this observation leads to differences in effectiveness where hypoxic tissue acts as if it has acquired a radiation resistance as reported in "Oxygen tension distributions are sufficient to explain the local response of human breast tumors treated with radiation alone" by Okunieff et al published in the International Journal of Radiation 1993, 26(4): 631-636.

The applicant has recognised the need for an improved model for high dose rate radiation treatments.

SUMMARY

According to the present invention there is provided an apparatus and method as set forth in the appended claims. Other features of the invention will be apparent from the dependent claims, and the description which follows.

We describe a computer system for analysing a radiation treatment plan using a dose of flash radiation to irradiate a volume within a patient, the computer system comprising a processor which is configured to obtain oxygen pressure information for the volume to be irradiated; obtain parameters from a patient treatment plan; input the obtained oxygen pressure information and parameters in to a model which predicts complex damage within the irradiated volume caused by the dose of flash radiation; output a prediction, using the model, of the complex damage caused within the volume by the dose of flash radiation; and quantify, using the prediction, a level of damage to healthy tissue within the irradiated volume; wherein complex damage is damage which is more complex than a double strand break within DNA in patient tissue and wherein the model is a function of energy of particles within the radiation and oxygen pressure which varies with time.

The parameters include modality of the flash radiation, magnitude of the dose, energy of the dose and pulse geometry of the dose. The pulse geometry may include the pulse length and instantaneous dose rate. The pulse geometry may be assumed to be rectangular. As explained below, this assumption is acceptable as long as the area under the curve defined by the pulse is the same because the oxygen level depends on the dose in a linear fashion. Another assumption which may be included is that the dose is delivered in a single pulse. The modality of the flash radiation may be selected from any suitable particle including electrons, photons, α particles and carbon particles.

The processor may be further configured to quantify the level of damage to healthy tissue relative to a level of damage caused by radiation which is not flash radiation and determine whether the dose of flash radiation would produce a sparing effect. Flash radiation uses ultra-high dose rates. Radiation which is not flash radiation may also be termed standard radiation and may be considered to be anything lower than 6 Gy per minute. A tissue sparing effect results in the therapy have a reduced effect on normal biological tissue but a constant effect on tumour. This beneficial effect of flash radiotherapy may be termed a flash effect. As explained below, we hypothesise that the flash effect occurs due to the environment reaching full hypoxic conditions and therefore a reduced generation of DNA-damage.

When it is determined that the treatment plan does not produce a sparing effect, the processor may be further configured to adjust at least one of the parameters obtained from the patient treatment plan and output the at least one adjusted parameters. For example, the processor may be further configured to adjust at least one of the parameters by: calculating a cost function based on the predicted complex damage; and applying an optimisation function to the calculated cost function to determine optimised parameters including at least one adjusted parameter.

The processor may be configured to output the prediction of complex damage in the form of a three-dimensional damage map $M_d[i,j,k]$. Each point within the 3D space defined by the map (or matrix) may be termed a voxel. The model may thus be considered to depend on the pulse geometry, pulse length instantaneous dose rate (i.e. Gy/ns) and total dose delivered in a single pulse in a voxel. Similarly, where the parameter includes the dose, information about the dose may be input as a three-dimensional map $D[i,j,k]$. The oxygen information (pressure or concentration) may also be input as a three-dimensional map $P[i,j,k]$.

The processor may be configured to predict complex damage caused by every single charged particle in each cell within the damage map by integrating the model over the energy spectrum, for example using:

$$M_d = D \int_0^{E_{max}} \Psi(E) F_d(P',E) dE$$

where D is a three-dimensional matrix of dose, $\Psi(E)$ is a dose depositing charged particle field and $P'=T(P)$ where P is a three-dimensional matrix of oxygen pressure information and T is a mapping which transforms spatial coordinates of P to match D.

Oxygen pressure may be considered to vary with time and may be expressed as:

$$p = p_0 - Rd$$

where the $p_0$ is the initial partial oxygen pressure and is expressed in terms of [$pO_2$ mmHg], d is the dose in Gy and the depletion rate R is expressed in terms of [$pO_2$ mmHg/Gy]. In other words, as an example, oxygen pressure may be expressed as a linear function of the delivered dose. This may be considered as a model for oxygen depletion. The model may be expressed as an oxygen dose histogram showing the delivered dose at each oxygenation level while the dose is being delivered. The surface under this first histogram may be equivalent to the total delivered dose. Alternatively, the model may be expressed as a dose oxygen histogram showing the oxygenation level at a sequence of values of the dose while the dose is being delivered. The dose oxygen histogram may be considered to be an inverse of the oxygen dose histogram.

Another assumption which may be incorporated into the model is that any oxygen repletion during the pulse is considered to be incorporated in the depletion rate R. In other words, we assume that the depletion rate constant R is much larger than any repletion rate. The processor may be configured to predict complex damage due to varying oxygen pressure in each cell within the damage map by integrating the model over time, for example using:

$$M_d = \int_0^T F_t(E, p(t)) dt$$

where $M_d$ is the damage map, $F_t$ is the model, E is energy and p(t) is the variation of oxygen pressure with time.

The model may be expressed as:

$$F_t(E, p) = \frac{g_4(p) - g_3(p)}{\pi} \left[ \arctan \frac{(g_1(p) - E)}{g_2(p)} \right] + g_3(p)$$

with $$g_i(x) = \frac{xa_i + b_i}{x + c_i} \text{ for } i \in \{1, 2, 3, 4\}$$

where
E is energy
p is oxygen pressure
x is a universal variable which represents oxygen,
$a_i$, $b_i$ and $c_i$ are real numbers determined by the type of flash radiation, e.g. using experimentation or simulation.

If all of the spectrum of dose depositing charged particles is in a low-LET regimen, the pressure dependence can be reduced to a single version:

$$g(x) = \frac{xa + b}{x + c}$$

where x is the partial oxygen pressure an the parameters, a, b, c, are determined for a single representative energy depending on the case.

The model may quantify damage due to oxygenation effects with an oxygen fixation mechanism which is expressed using set theory in which there is a set L of damaged regions within the patient tissues, within the set L there is a subset C of damaged regions which are classified as complex and within the subset C, there is a subset P of complex damaged regions which are fixated by oxygen, a subset R of complex damaged regions which are repairable by chemical repair and a subset $C_R$ of complex damaged regions which remain to be repaired by biological repair. The number of complex damaged regions within the subset $C_R$ may be proportional to the number of damaged regions within the subset P. The oxygen fixation mechanism may determine the number of damaged regions within the subset P using a differential equation which defines saturation behaviour. The relationship between $C_R$ and P may be transformed linearly to reduce the number of variables to three parameters, for example by multiplying by the initial slope of the differential equation.

The model above is very effective in modelling the DNA damage by quantifying the oxygenation effect on DNA-damage based on the oxygen fixation mechanism which is in competition with the chemical repair. As explained in more detail in the examples below, the flash effect does not typically occur below a threshold dose (e.g. 6 Gy for normal tissue). The flash effect also depends on the relative LET of a particle field. The flash effect depends on the initial oxygen levels in the irradiated tissue but these are not typically adjustable. Accordingly, the parameters of the radiation system may need to be adapted to account for the oxygen levels.

The computer system may comprise the processor as described above and a memory coupled to the processor. The memory may store computer-executable instructions therein which when executed by the computer system cause the processor to carry out the steps described above. We also described a non-transitory computer-readable storage medium having computer-executable instructions for causing a computing system (and processor therein) to perform the steps described above.

The computer system may also be incorporated in a radiation treatment system. Thus, we also describe a radiation treatment system comprising the computer system described above, a radiation system for applying a radiation treatment; and a control system for controlling the radiation system, wherein the computer system is configured to control the radiation system by outputting parameters to be implemented by the radiation system. The radiation treatment system may further comprise storage storing the patient treatment plans.

We also describe a method for analysing a radiation treatment plan using a dose of flash radiation to irradiate a volume within a patient, the method comprising obtaining oxygen pressure information for the volume to be irradiated; obtaining parameters from a patient treatment plan; inputting the obtained oxygen pressure information and parameters in to a model which predicts complex damage within the irradiated volume caused by the dose of flash radiation; outputting a prediction, using the model, of the complex damage caused within the volume by the dose of flash radiation; and quantifying, using the prediction, a level of damage to healthy tissue within the irradiated volume; wherein complex damage is damage which is more complex than a double strand break within DNA in patient tissue and wherein the model is a function of energy of particles within the radiation and oxygen pressure which varies with time.

We also describe a method of deriving a radiation treatment plan comprising the method of analysing a radiation treatment plan as described above, adjusting at least one of the parameters obtained from the patient treatment plan and outputting the at least one adjusted parameters.

As will be appreciated by one skilled in the art, the method described above may be embodied as a system, or computer program product. Accordingly, present techniques may take the form of an entirely hardware embodiment, an entirely software embodiment, or an embodiment combining software and hardware aspects. Furthermore, the present techniques may take the form of a computer program product embodied in a computer readable medium having computer readable program code embodied thereon. The computer readable medium may be a computer readable signal medium or a computer readable storage medium. A computer readable medium may be, for example, but is not limited to, an electronic, magnetic, optical, electromagnetic, infrared, or semiconductor system, apparatus, or device, or any suitable combination of the foregoing.

Computer program code for carrying out operations of the present techniques may be written in any combination of one or more programming languages, including object-oriented programming languages and conventional procedural programming languages. Code components may be embodied as procedures, methods, or the like, and may comprise sub-components which may take the form of instructions or sequences of instructions at any of the levels of abstraction, from the direct machine instructions of a native instruction set to high-level compiled or interpreted language constructs.

Embodiments of the present techniques also provide a non-transitory data carrier carrying code which, when implemented on a processor, causes the processor to carry out any of the methods described herein.

The techniques further provide processor control code to implement the above-described methods, for example on a general-purpose computer system or on a digital signal processor (DSP). The techniques also provide a carrier carrying processor control code to, when running, implement any of the above methods, in particular on a non-transitory data carrier. The code may be provided on a carrier such as a disk, a microprocessor, CD- or DVD-ROM, programmed memory such as non-volatile memory (e.g. Flash) or read-only memory (firmware), or on a data carrier such as an optical or electrical signal carrier. Code (and/or data) to implement embodiments of the techniques described herein may comprise source, object, or executable code in a conventional programming language (interpreted or compiled) such as Python, C, or assembly code, code for setting up or controlling an ASIC (Application Specific Integrated Circuit) or FPGA (Field Programmable Gate Array), or code for a hardware description language such as Verilog® or VHDL (Very high-speed integrated circuit Hardware Description Language). As the skilled person will appreciate, such code and/or data may be distributed between a plurality of coupled components in communication with one another. The techniques may comprise a controller which includes a microprocessor, working memory and program memory coupled to one or more of the components of the system.

Although a few preferred embodiments of the present invention have been shown and described, it will be appreciated by those skilled in the art that various changes and modifications might be made without departing from the scope of the invention, as defined in the appended claims.

BRIEF DESCRIPTION OF DRAWINGS

For a better understanding of the invention, and to show how embodiments of the same may be carried into effect, reference will now be made, by way of example only, to the accompanying diagrammatic drawings in which:

FIG. 3b is an output damage map generated by the system of FIG. 3a;

FIG. 3c is a flowchart illustrating the steps of the method which may be applied in the treatment system of FIGS. 1 and 3a;

DETAILED DESCRIPTION OF DRAWINGS

Figure 1:
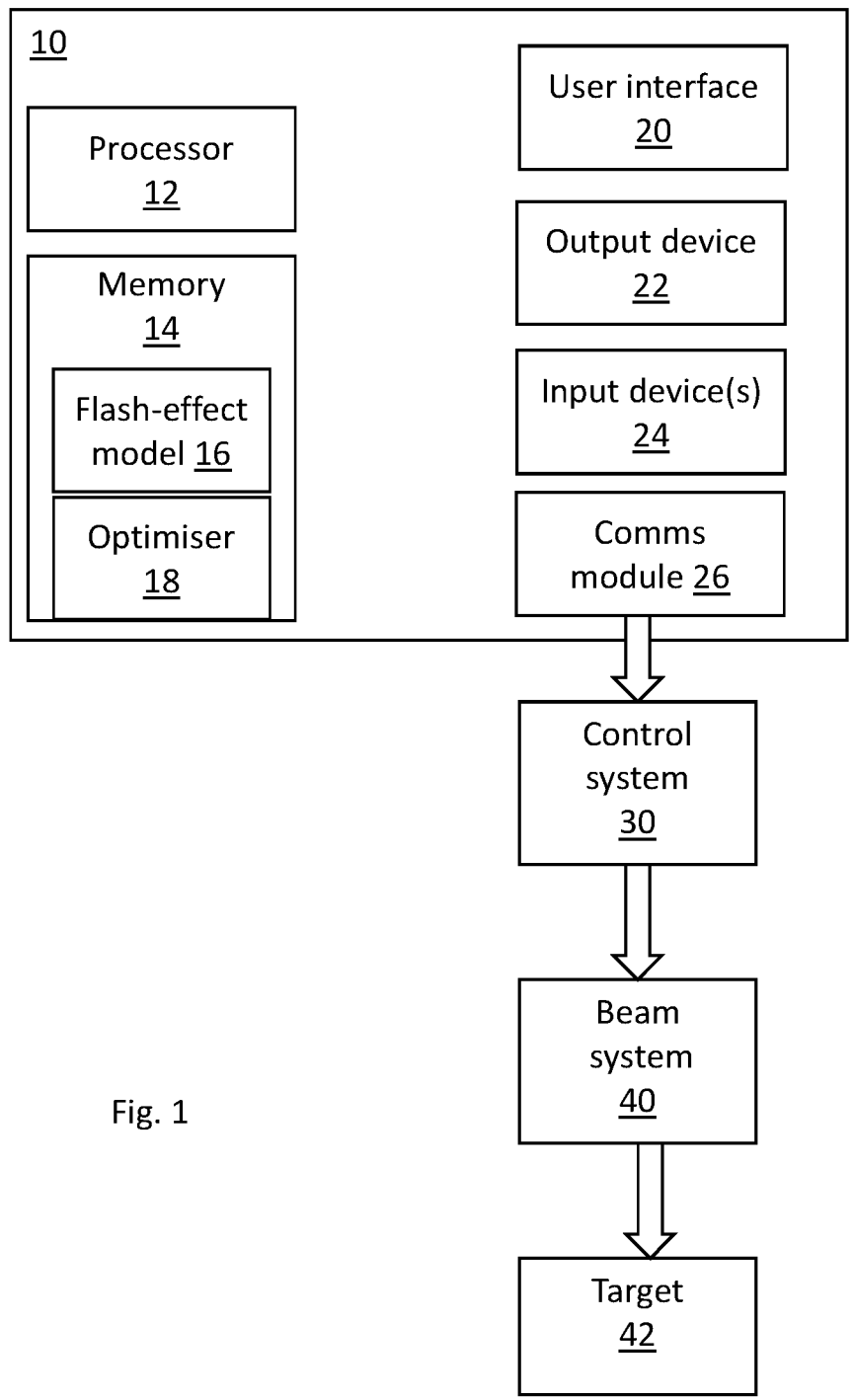
FIG. 1 is a schematic block diagram showing the components of a treatment system.

FIGS. 1a and 1b illustrate an example system for radiation treatment such as flash radiotherapy. The system comprises a computing system 10 which includes standard components including a processor 12 and memory 14. Computer executable instructions, such as program modules, are illustrated as residing within the memory 14 although it will be appreciated that these modules may reside in any computer storage media used by the system or distributed over networked computers. The memory may include volatile and non-volatile, removable and non-removable media implemented in any known way. For example, it may include but is not limited to random access memory, read only memory, electrically erasable programmable memory, flash memory or other storage.

The illustrated program modules include a flash effect model module 16 which models the effect of the dose applied by the radiation treatment and an optimiser module 18 which uses the results of the model to suggest changes to the treatment plan based on the model outputs. The model is described in more detail below.

The computing system 10 may also include other standard components including but not limited to a user interface 20, output device(s) 22, input device(s) 24 and a communications module 26. The user interface 20 may be in any standard form, e.g. a keyboard, mouse, voice input device, touch input device etc. Similarly, the output device 22 may be in any standard form such as a display to illustrate the results of the modelling and proposed treatment plan changes. The input device(s) 24 input information about the radiation system and the inputs are shown in more detail in FIG. 1b. The communications module 26 is used to connect the computing system 10 to other components, e.g. a control system 30 which is used to control a beam system 40 which applies radiation to a volume 42 within a patient (the irradiated volume) which typically includes a target and healthy tissue surrounding the target.

The flash effect model is used to model complex damage in DNA material, e.g. damage which is more complex than a double strand break. The derivation of the model is described in more detail below. In summary, the model incorporates a relationship quantifying the oxygenation effect on DNA-damage based on the oxygen fixation mechanism that is in competition with chemical repair. This relationship is then used in a model describing the dose dependent oxygen depletion within an ultra-high dose pulse. The model depends on the pulse geometry, pulse length, instantaneous dose rate (i.e. Gy/ns), total dose delivered in a single pulse and initial oxygen level in a voxel (point in 3D space).

The FLASH effect is quantified by taking into account the varying levels of oxygen concentrations during the pulse delivery. To do this we need an expression that combines energy and oxygen levels to quantify the induced damage at any point in time. The model F may be expressed as a function of energy E and oxygen pressure p and may have the following form:

$$F_t(E, p) = \frac{g_4(p) - g_3(p)}{\pi}\left[\arctan\frac{(g_1(p) - E)}{g_2(p)}\right] + g_3(p)$$

with $$g_i(x) = \frac{xa_i + b_i}{x + c_i} \text{ for } i \in \{1, 2, 3, 4\}$$

where
E is the energy
p is the oxygen pressure which is a function of time as defined below
x is a universal variable which represents the scarce resource (in this case oxygen),
$a_i$, $b_i$ and $c_i$ are real numbers The parameters, $a_i$, $b_i$ and $c_i$, are determined from cell experiments or alternatively from micro-dosimetric Monte Carlo simulations as described for example in "Effects of radiation quality and oxygen on clustered DNA lesions and cell death" by Stewart et al published in Radiat Res 176, 587-602 in 2011. Merely as an example, for an electron beam, the table below gives indicative values for a, b and c

|   | 1      | 2       | 3        | 4      |
|---|--------|---------|----------|--------|
| a | 42.686 | −3.599  | 0.000370 | 15.575 |
| b | 2.347  | 2.473   | 0.774    | 0.964  |
| c | 81.427 | 0.000328 | 0.000109 | 8.409 |

The parameter p is a function of time and a simple model is described in "An experimental and analytical study of oxygen depletion in stirred cell suspensions" by Whillans et al published in Radiation Res 84, 97-114 (1980) proposed a linear model for oxygen depletion:

$$p = p_0 - Rd$$

where the $p_0$ is the initial partial oxygen pressure and is expressed in terms of [$pO_2$ mmHg], d is the dose in Gy and the depletion rate R is expressed in terms of [$pO_2$ mmHg/Gy]. Rates between 0.21 and 0.42 mmHg/Gy have been observed. Using this equation allows every nanosecond to be associated with a specific oxygen pressure. As described in more detail below, there may be various assumptions when implementing the model. For example, one assumption may be that any oxygen repletion is considered to be incorporated in an effective depletion constant. This assumes that the depletion rate constant R is much larger than any repletion rate.

The model also suggests that the flash effect may result from a full depletion of oxygen within the irradiated tissue, leading to a hypoxic environment. This provides a protective environment for part of the dose deposition.

The equation above may be expressed as:

$$[O_2] = [O_2]_0 - Rd$$

where the $[O_2]$ is the oxygen depletion, $[O_2]_0$ is the initial partial oxygen pressure and is expressed in terms of [$pO_2$ Torr], d is the dose in Gy and the depletion rate R is expressed in terms of [$pO_2$ Torr/Gy]. It may be difficult to transpose this to an ultra-high dose rate regimen where we would apply this depletion within the fine pico-second structure of a pulse. This is because oxygen depletion is not instantaneous, but rather the result of a cascading process initiated by the generation of radicals in a complex process taking several nano-seconds (ns).

Indeed, "Time scale of radiation-induced oxygen depletion and decay kinetics of oxygen-dependent damage in cells irradiated at ultrahigh dose rates" by Ling published in 1975 in Radiat. Research 63, 455-67 proposed a theoretical analysis of oxygen depletion in ultra-high dose rate regimen by positing a depletion by interaction of the available oxygen with any radiation induced lesion (including DNA-lesions). Interestingly, the paper decouples the direct ionisation process from the oxygen depletion process, considering the first as a trigger of a cascade process (which includes the generation of indirect damage). The interaction of the available oxygen, with any induced species, is modelled as a second order reaction. The time dependent concentration, starting from an initial concentration $[O_2]_0$ then becomes:

$$[O_2(t)] = \frac{\{GD[O_2]_0 - [O_2]_0^2\}e^{\lambda([O_2]_0 - GD)t}}{GD - [O_2]_0 e^{\lambda([O_2]_0 - GD)t}}$$

The quantity denoted by λ is the binding rate of the oxygen to any lesion. The delivered dose D impacts the medium by generating a concentration of radiation induced species with a rate of G per dose unit.

Rather than trying to model the complete process in a time dependent manner an abstraction is made. It is observed that a range of oxygenation levels present during the dose deposition process, which is a protracted process in itself. Both oxygen depletion and the dose deposition process take place in a time resolution of the order of nano-seconds.

This process can be subdivided in delivered dose quanta, each at a given oxygenation level. This can be abstracted by creating a histogram such as the one shown in FIG. 2a, where the delivered dose is given as a function of the oxygenation levels present throughout the dose delivery. Positional information is lost because it is plotted as a histogram. The only information is the instantaneous dose deposition under given oxygenation conditions wherever and whenever (within the pulse) this occurs. Thus, as shown, most of the dose (nearly 12 Gy) is delivered when there is full oxygen depletion. Thereafter, the same small amount of dose is delivered for each other level of oxygen pressure (measured at increments of 1 Torr). This subtle difference resolves the problem that the oxygenation fixation deals with oxygen removal in the immediate vicinity of the DNA-strand (i.e. a few nano-meters) while oxygen depletion takes place over the whole of the irradiated volume. The surface under this Oxygenation Dose Histogram (ODH) is then the total delivered dose.

The generation of these histograms may be done by Monte Carlo simulations of the oxygen depletion model, an analytical expression, or by experimental results. All of these methods may also be used to generate the inverse histogram which may be termed a Dose Oxygen Histogram and an example is shown in FIG. 2b. FIG. 2b shows that the partial oxygen pressure drops by 0.6 Torr for each of the first seven dose levels, namely 0.6, 1.8, 3, 4.2, 5.4, and 6.6 Gy. For the remaining dose levels (each incrementing by 1.2 up to 15 Gy), there is no further depletion of the oxygen level because there is full hypoxia already.

Figure 2A:
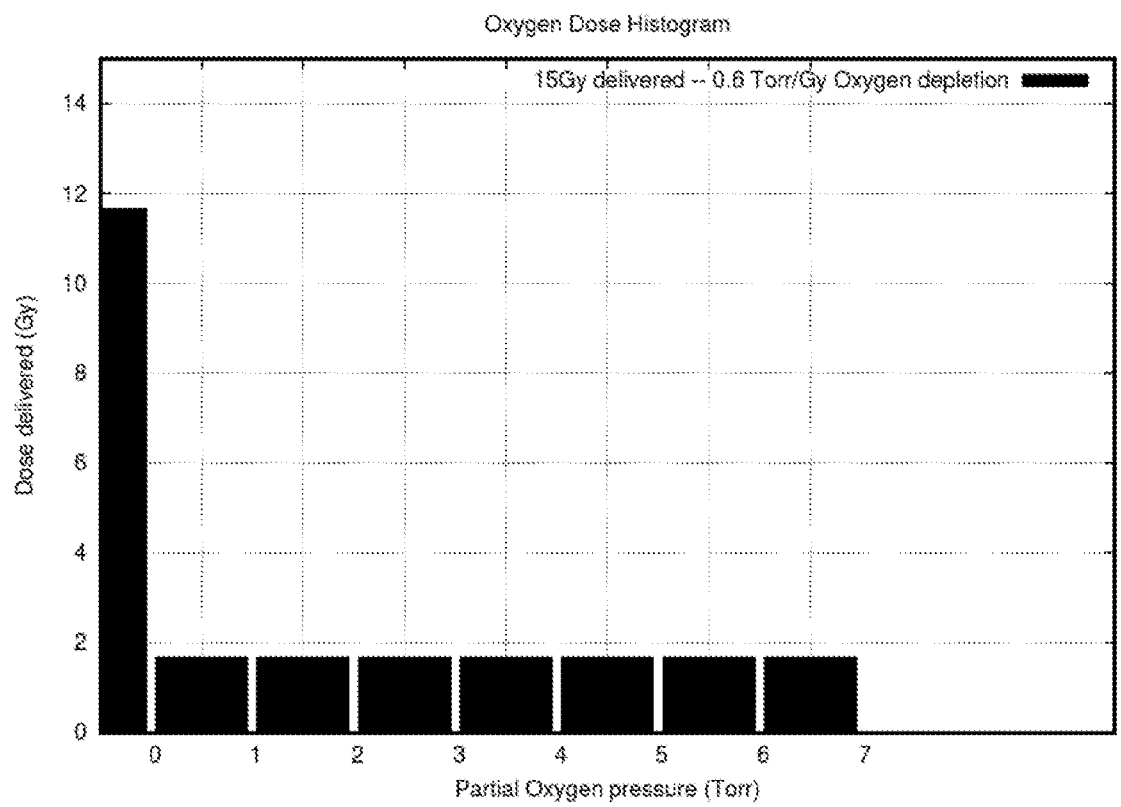
FIG. 2a is a histogram plotting the partial oxygen pressure (Torr) for different values of a dose (Gy) which are delivered.
Figure 2B:
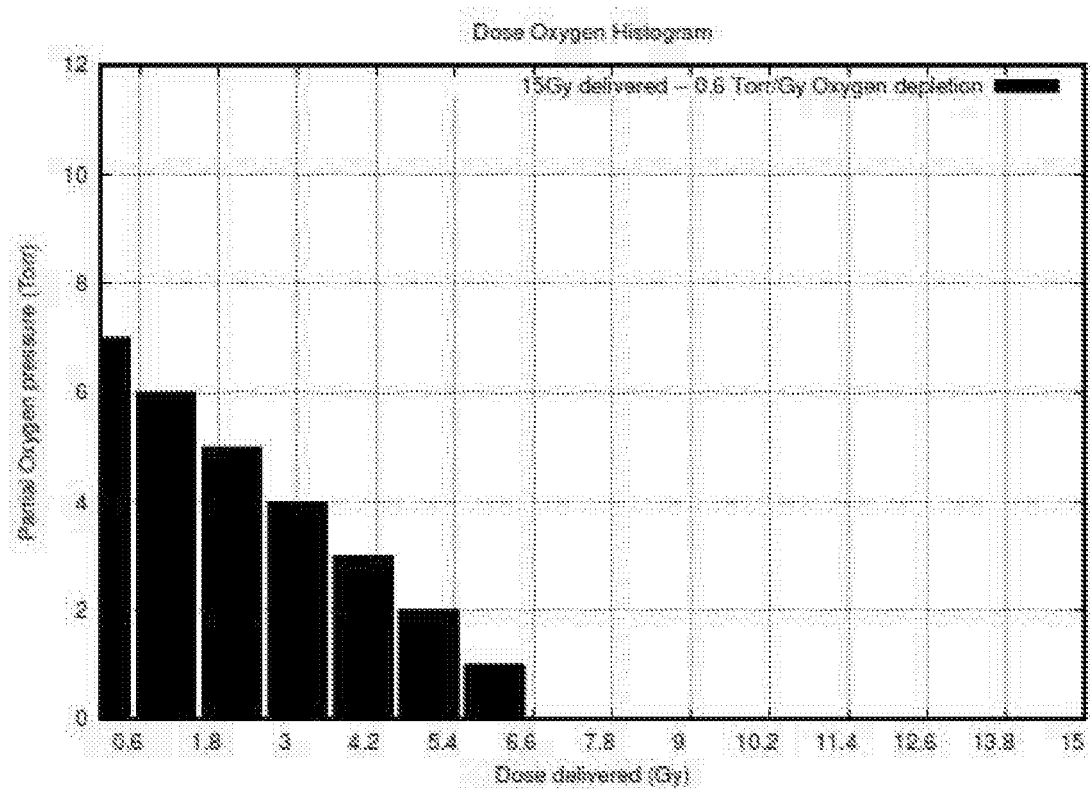
FIG. 2b is a histogram plotting the dose delivered (Gy) for different values of partial oxygen pressure (Torr)

FIGS. 2a and 2b are plotted based on a linear dose depletion of 0.6 Torr/Gy while delivering 15 Gy. It is important to note that the latter is a specific way of generating the ODH, but not the only one or correct one. Note that in the ODH, a substantial part of the dose is delivered in complete hypoxia. The oxygen dose histogram may be considered to provide an instantaneous oxygen level at a delivered dose. The histogram concept may alleviate the need for a mechanistic approach. At each given oxygen level, the oxygen fixation concept is used to calculate the change in DNA-damage induction compared to the fully hypoxic case. Using the ODH concept, it may be possible to estimate the effect even in multiple pulsed cases.

The ODH is then converted to a total complex damage count which may be termed $M_D$ (or $F_d(E,p)$ in the terminology above) which can be readily compared to a damage count in a case where no change in oxygenation takes place $(M_{D0})$. The ratio $M_D/M_{D0}$ then provides a quantification of the FLASH effect which is always lower than 1, and therefore is a sparing effect.

An interesting property of ODHs, in contrast with the more intuitive DOH, is that they are additive, facilitating the implementation of pulsed treatments with partial depletion and/or incomplete re-oxygenation. Indeed, if a subsequent pulse with a different oxygenation signature is delivered, both ODHs can simply be added together and the calculation can then be performed. A special case is when complete (local) re-oxygenation occurs between pulse and the histogram is added to itself.

Figure 2C:
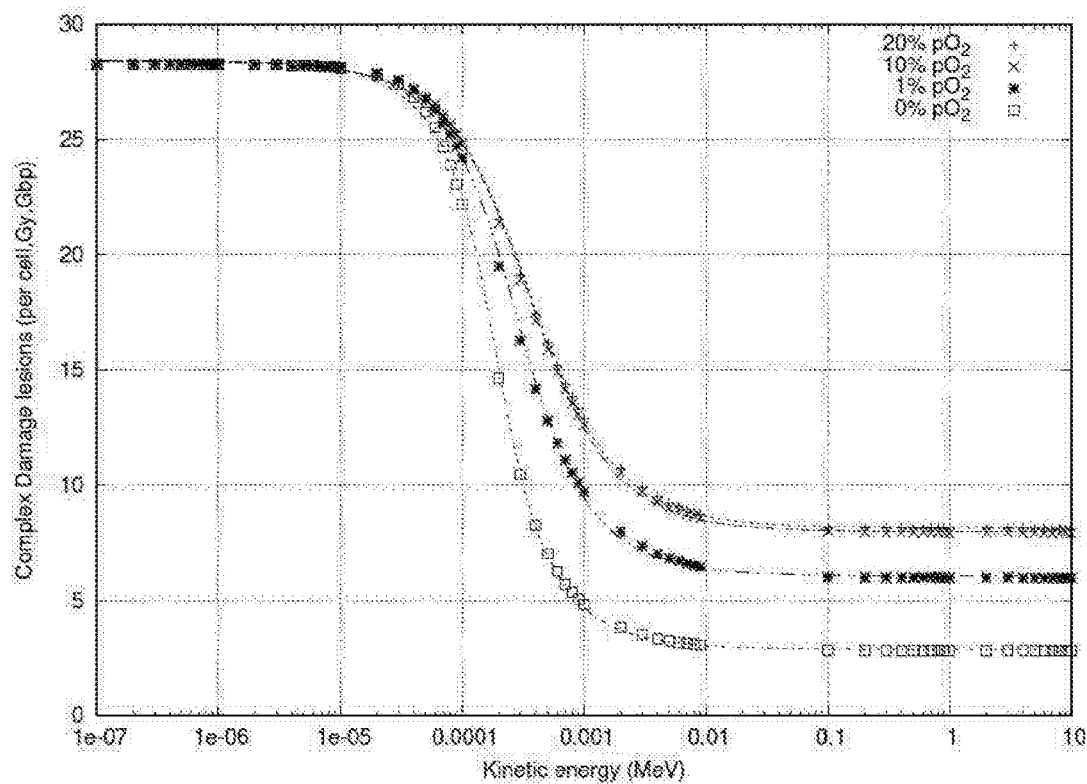
FIGS. 2c and 2d each plot the number of lesions having complex damage for different levels of oxygen concentration as a function of energy as modelled by the system in FIG. 1.
Figure 2D:
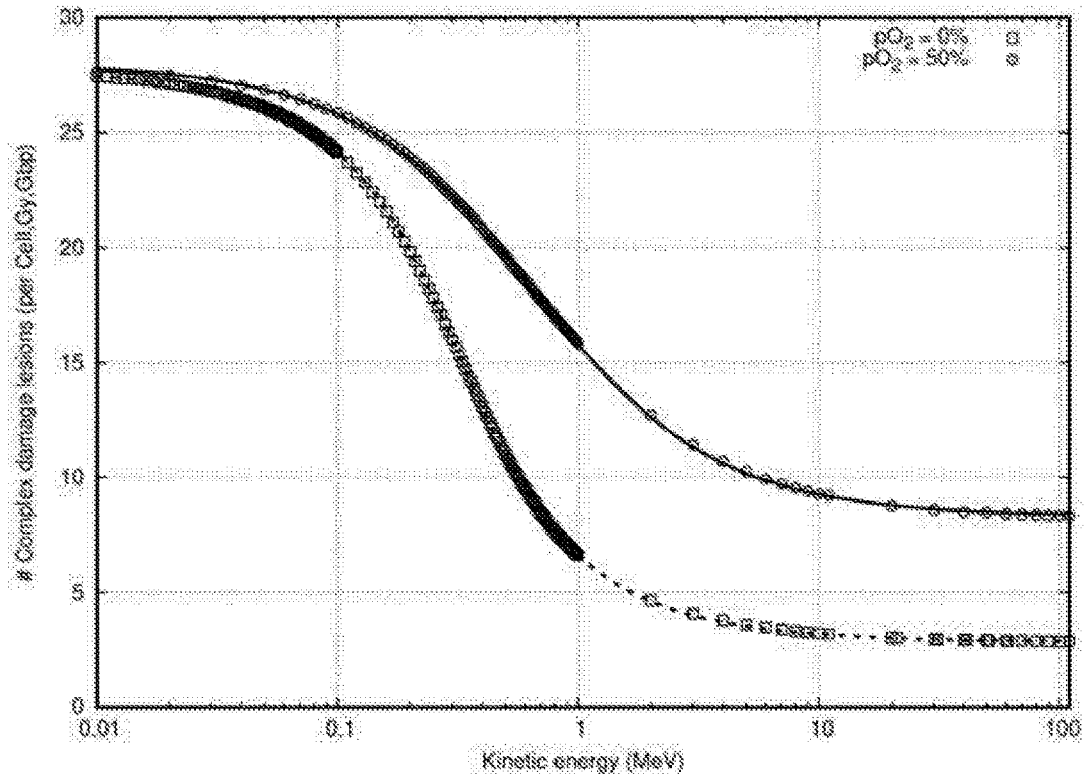

FIG. 2c plots the complex damage as modelled by the function $F_d(E,p)$ against different values of energy for four different oxygen concentration levels, namely anoxic (0%), 1%, 10% and fully oxygenated (20%). Similarly, FIG. 2d plots the complex damage as modelled by the function $F_d(E,p)$ against different values of energy for anoxic (0%) and hyperbaric (50%) oxygen conditions. In FIGS. 2c and 2d, the lines are calculated by the model and the points are calculated by another method, namely the Monte Carlo damage simulation code (MCDS) described in "Effects of radiation quality and oxygen on clustered DNA lesions and cell death" by Stewart et al published in Radiat Res 176, 587-602 in 2011. As shown in FIGS. 2c and 2d, the modelled values are flat with respect to variations in energy for low-LET modalities. As a consequence, if all of the spectrum of dose depositing charged particles is in a low-LET regimen, the pressure dependence can be reduced to a single version:

$$g(x) = \frac{xa + b}{x + c}$$

where x is the partial oxygen pressure and the parameters, a, b, c, are determined for a single representative energy depending on the case.

Figure 2E:
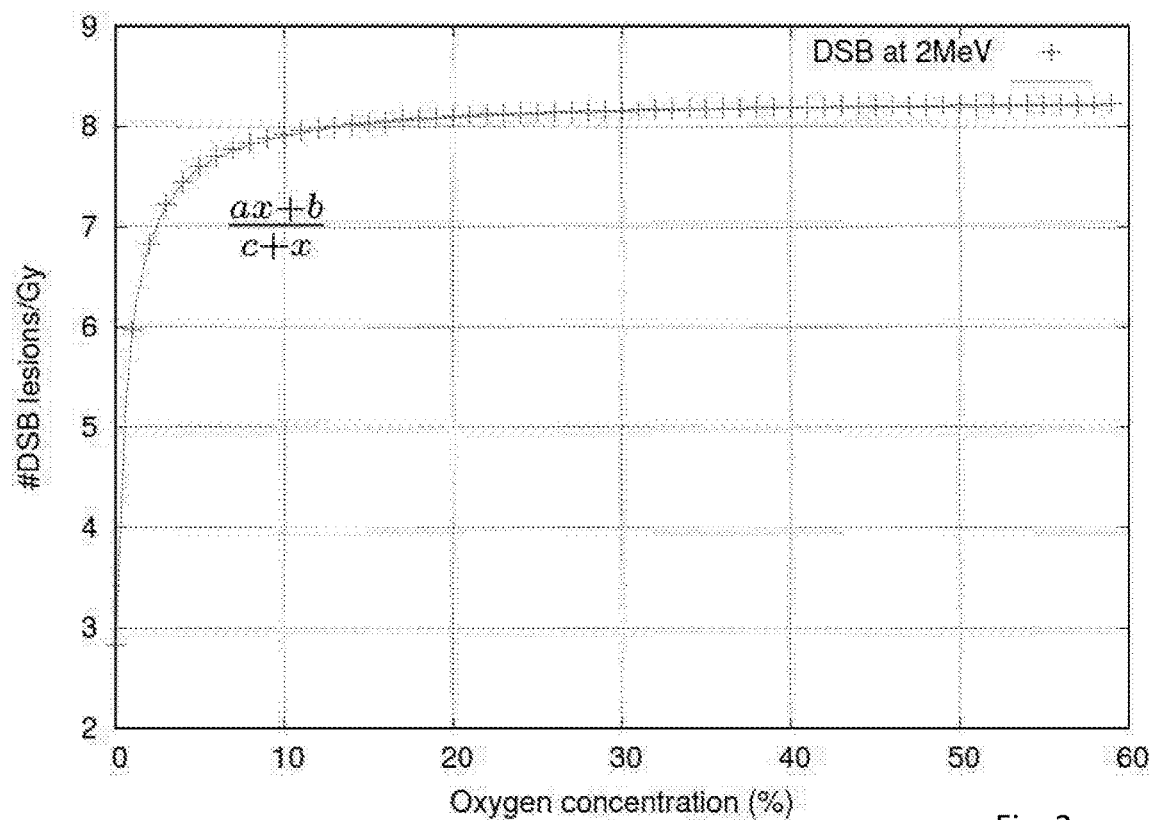
FIGS. 2e and 2f plots the number of lesions having complex as a function of oxygen concentration as modelled by a simplified version of the model in the system in FIG. 1 having different parameter values.
Figure 2F:
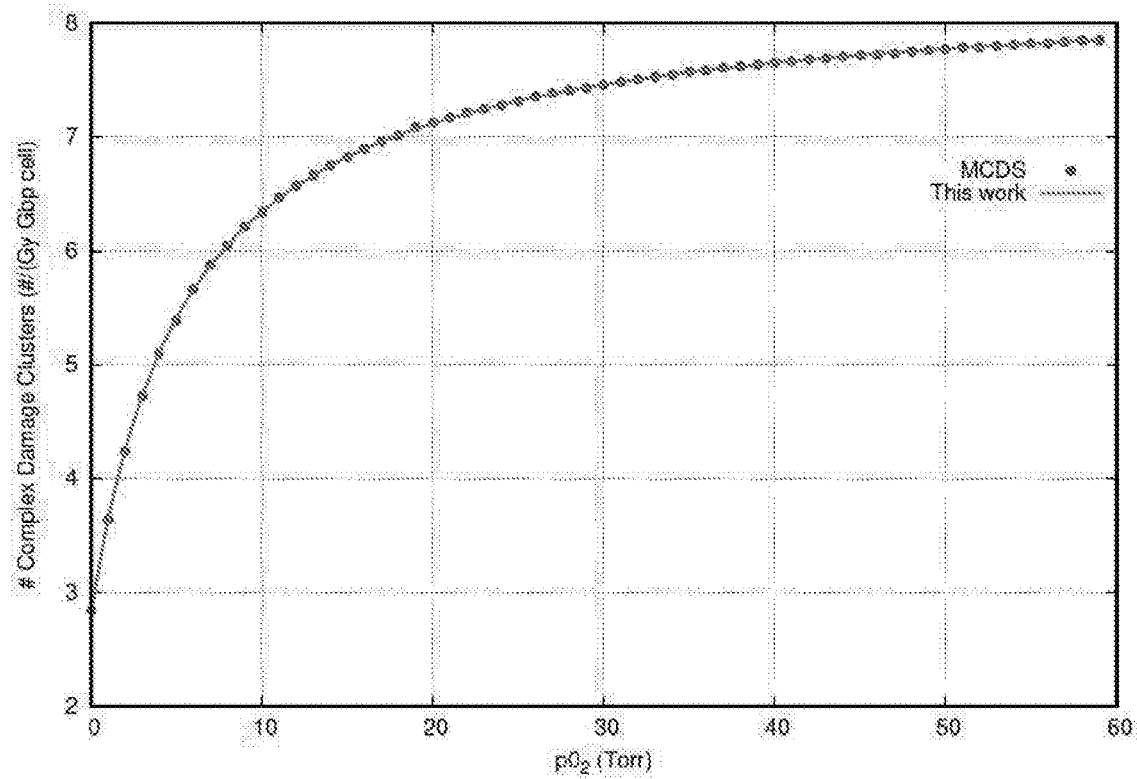

This simplified equation is valid for electron treatments as well as photon irradiation which is a deposition of secondary electrons. Thus it is sufficient to express the partial oxygen pressure as a percentage of normal atmospheric pressure. FIG. 2e plots the number of (complex damage) lesions against oxygen concentration using the simplified equation above. FIG. 2f is an alternative plot of the number of complex damage clusters against oxygen concentration. In the example of FIG. 2f, the values of a, b and c are 8.334±0.002, b=15.99±0.07 and c=5.67±0.02. As for FIGS. 2c and 2d, the lines are calculated by the model and the points are calculated by the MCDS algorithm. In both FIGS. 2e and 2f, there is a plateauing of the number of clusters as the oxygen concentration increases. It is noted that in radiobiology, the quantification of partial oxygen pressure is reported as a percentage (see FIG. 2e). In clinical practice, tissue oxygenation levels are reported in millimetres of mercury pressure (mmHg). This is a better measure because levels are of the order of 20 mmHg ($pO_2$) in well-oxygenated tissue and 100 mmHg ($pO_2$) in arterial blood. The more precise unit of Torr (1 Torr approximates to 1 mmHg) is used in FIG. 2f.

Figure 3A:
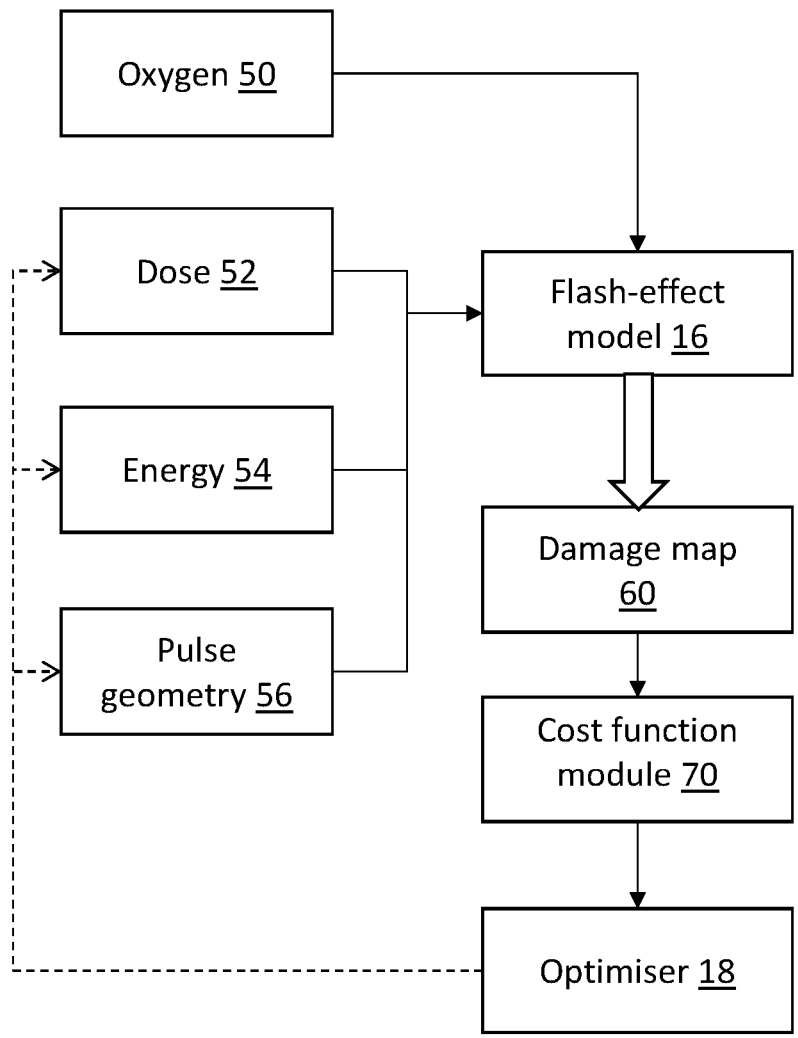
FIG. 3a is a schematic diagram illustrates the inputs and outputs within part of the treatment system.

FIG. 3a illustrates more detail regarding the inputs to and outputs from the computing system. As shown, the inputs include information about initial oxygen concentration 50 and information about the radiation therapy itself including dose 52, energy 54 and pulse geometry 56. The inputs are used by the flash-effect model 16 to output information on the damage which will be caused by the application of the treatment. The oxygen concentration is the oxygen concentration at the location of the radiated volume, i.e. within the patient. The oxygen concentration may be measured using any known technique. The oxygen concentration typically varies from patient to patient and from organ to organ within a patient. Oxygen concentration may be expressed in percentage or in partial oxygen pressure. The oxygen concentration is not a parameter which may not typically be varied as it is an inherent property of the patient.

The total dose may be considered to be delivered in a single pulse. Pulse lengths are typically of the order of a few s. Due to these orders of magnitude it is convenient to define a new quantity, the instantaneous dose rate $\dot{D}$, expressed in cGy/ns (an explanation for the conversion of Gy to cGy is provided below). The area under a pulse represented in a dose rate versus time graph is the total dose delivered in a single pulse. Thus:

$$D = L \times \dot{D}$$

where D is the instantaneous dose rate and L is the pulse length.

In the case, where the dose rate is not constant (i.e. the pulse shape is not rectangular):

$$D=\int_0^L \dot{D}(t)dt$$

This implies that for instance, a dose of 15 Gy in a single 3.4 μs pulse in the rectangular case has an instantaneous dose rate of 0.44 cGy/ns. The oxygen level depends on the dose in a linear fashion and thus a rectangular pulse is equivalent to any other shape, as long as the area under the curve is the same. Accordingly, the input pulse geometry may be simplified by considering the dose pulse to be rectangular in shape with a given height or instantaneous dose rate $\dot{D}$ and pulse length L.

The radiation is typically applied as a spectral beam. Accordingly, the output from the model may be in the form of a three-dimensional damage map or matrix $M_d[i,j,k]$ where each point of the map may be known as a voxel. The oxygen concentration information may be input as a 3-dimensional matrix representing the oxygen concentration $P=\rho[i,j,k]$ and similarly information about the dose may be input as a 3-dimensional matrix $D=D[i,j,k]$. Assuming there is a mapping T which transforms the spatial coordinates of P to match those of D, then the equation above may be used to define the damage map for a given particle and energy E as:

$$M_d=M_d[i,j,k]=D\circ F_d(P',E)$$

where $P'=T(P)$, $\circ$ denotes the Hadamard or elementwise product,

Dose deposition spectra are by definition not monoenergetic and do not consist of single modalities. For any radiation source with a given energy spectrum, a dose depositing charged particle field $\Psi(E)$ exists in every voxel (i.e. at every point in 3D space defined by the matrices). This is the dose deposited by charged particles of energy E. Using Monte Carlo simulations, it is possible to calculate this field and spectrum in every voxel. The final effect $M_d$ in each voxel $[i,j,k]$ can now be calculated by integrating over the spectrum as $F_d(E,p)$ to calculate the damage contribution of every single charged particle energy. Accordingly, the damage contribution may be calculated per cell, per Gy and per Giga base pair (factoring the length of the DNA strings into the equation) as:

$$M_d=D\int_0^{E_{max}}\Psi(E)F_d(P',E)dE$$

This may alternatively be expressed as:

$$M_d = \frac{\int_0^\infty \Psi(E)D\circ F_d(P',E)dE}{\int_0^\infty \Psi(E)dE}$$

The expression above may be normalised to damage levels where 1 Gy provides a single double strand break per cell per Giga base pair.

The model has two variables: energy and oxygen pressure (which is varying with time). Thus, in addition to considering the variation due to energy, for a single energy of a specific particle, the damage contribution may be calculated per cell, per Gy and per Giga base pair (factoring the length of the DNA strings into the equation) as:

$$M_d=D\int_0^T F_t(E,p(t))dt$$

Figure 3B:
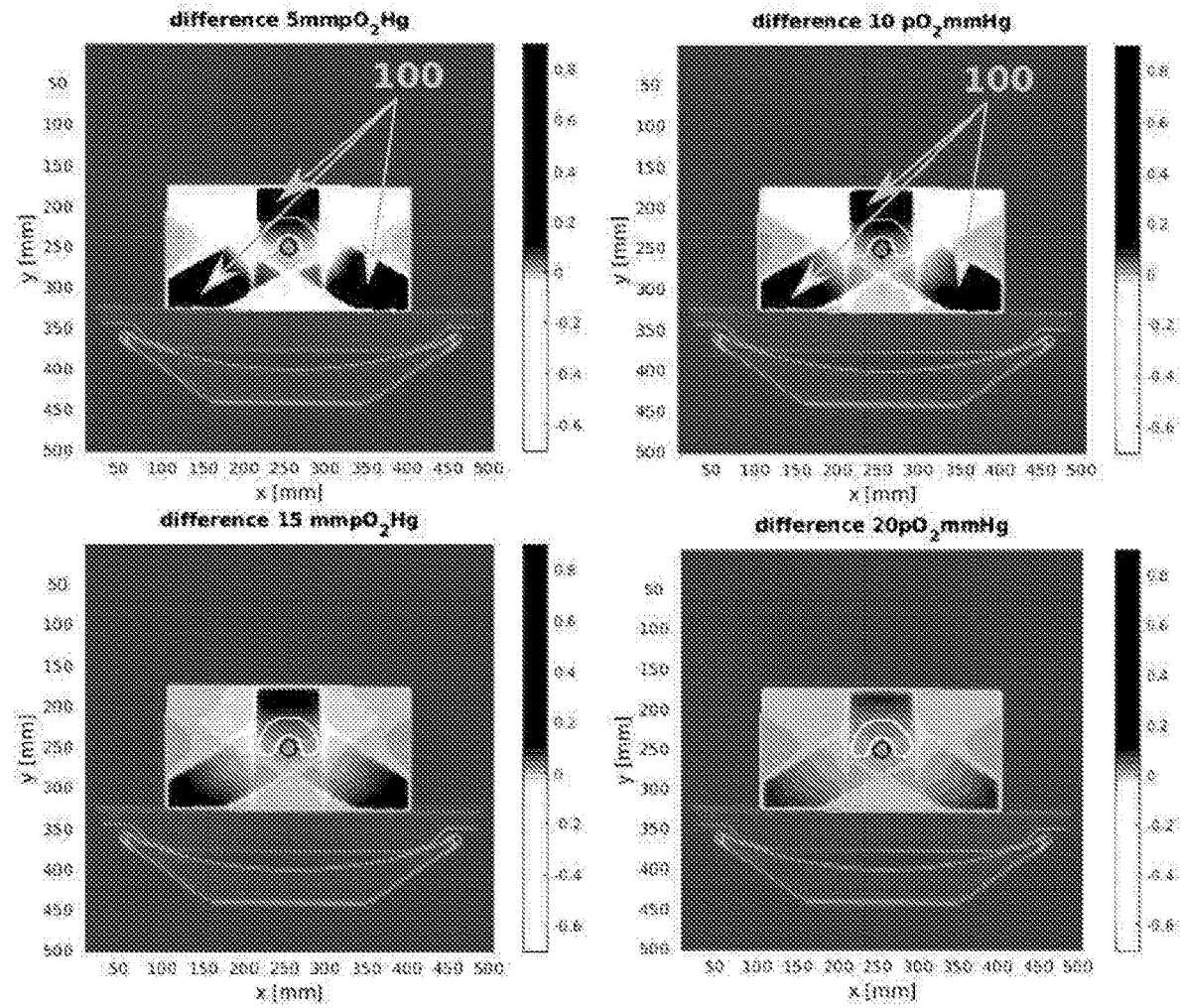

The model is applied to generate the information on the damage caused by the proposed treatment. As shown in FIG. 3b, the damage information may be output as a damage map 60 which as shown may be expressed in terms of the relative effect of the flash treatment relative to standard treatment (rather than as a quantitative amount of damage). In FIG. 3b, increased sparing effect is shown in red (i.e. as labelled 100). Each of the examples in FIG. 3b is for a treatment system comprising three photon beams delivering 6 Gy at their maximal point of convergence in the centre of the target in a rectangular box. The beams are delivered consecutively in time so the sum of the beams does not contribute to the flash effect. For example, there may be a single beam which is rotated on a gantry to provide radiation from three different angles. For each beam, the flash effect only occurs outside of the target. The results are modelled at four different oxygenation levels, 5 mmHG $pO_2$, 10 mmHG $pO_2$, 15 mmHG $pO_2$ and 20 mmHG $pO_2$. There is increased sparing effect at lower oxygen levels.

The damage map may be input to a cost function module 70 which calculates the cost associated with the treatment and the resultant damage. Any suitable cost function may be applied. Typically cost functions use dose but in this application, the damage may be used in the cost function. An example cost function is described in "The physical basis of IMRT and inverse planning" by S Webb The British Journal of Radiology 2003 76:910, 678-689.

The cost function may then be used in an optimiser module 18 which provides feedback to alter one or more of the dose, energy or pulse geometry to improve the treatment, e.g. by minimising the damage. Any suitable optimisation may be applied, e.g. least squares, steepest descent, simulated annealing and split feasibility problem resolution. An example of a steepest descent algorithm is described in "Implementation of a new optimization algorithm in VMAT for the treatment of prostate cancer" by Birba et al published in Physica Medica, Volume 44, Supplement 1,201 Pages 38-39, 2017. An example of simulated annealing is described in "Multiple local minima in radiotherapy optimization problems with dose-volume constraints" by Deasy et al published in Med. Phys. 241157-61 or "Sequential annealing-gradient gamma-knife radiosurgery optimization" by Ove et al published in Phys. Medicine Biol. 48, 2071-2080, 2003. An example of a split feasibility problem resolution algorithm is described in "Dynamic string-averaging cq-methods for the split feasibility problem with percentage violation constraints arising in radiation therapy treatment planning" by Brooke et al published in 2019. It is noted that some optimisation algorithms do not use a cost function, e.g. split feasibility and the cost function is not essential to obtain an adjusted parameter(s).

Figure 3C:
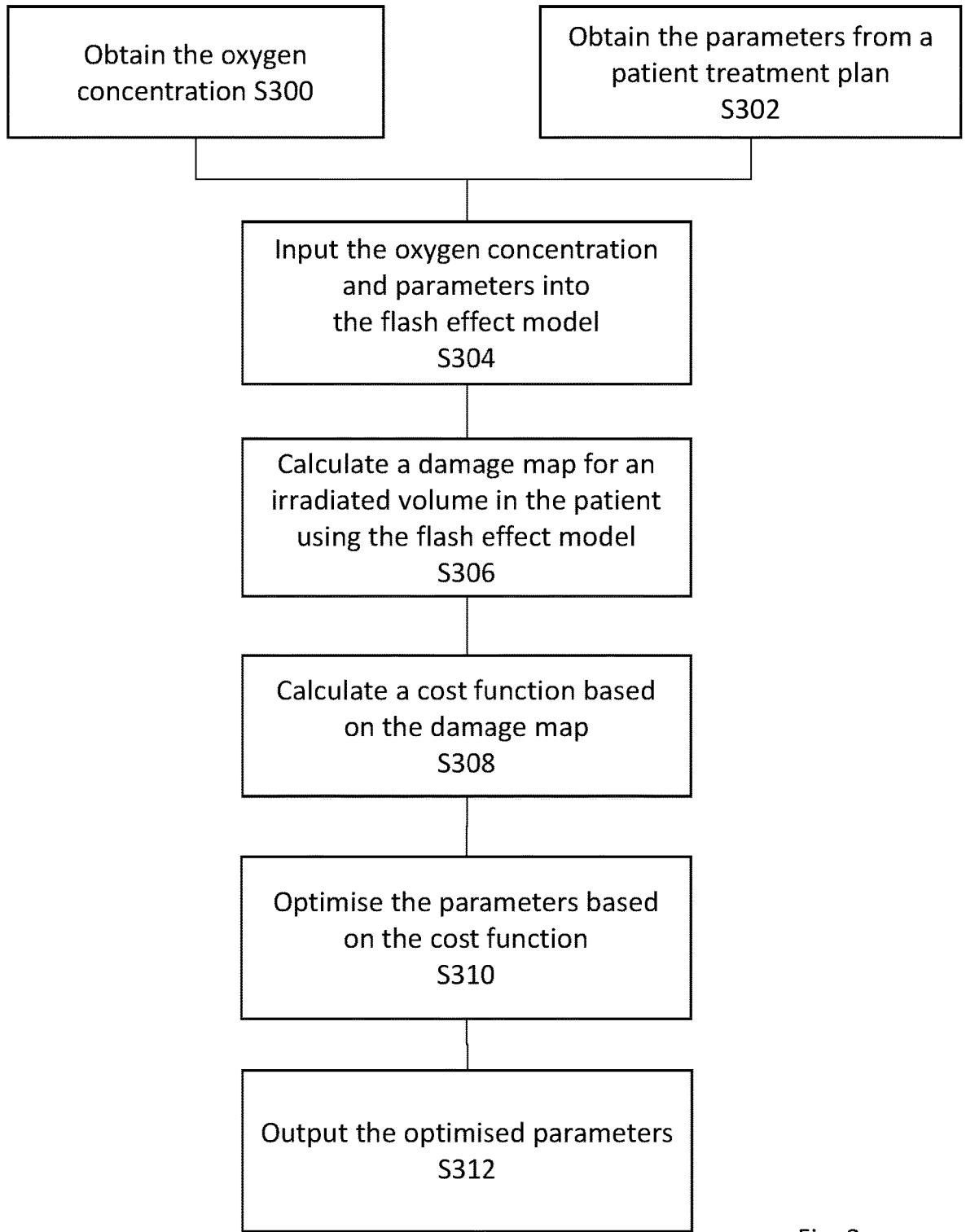

FIG. 3c shows the steps of a method which may be used in the system described above to improve or alter a treatment plan for a patient. In a first step, the oxygen concentration level for the volume in the patient which is to be irradiated are obtained (step S300). The oxygen concentration level may be measured using any known technique. The relationship between oxygen concentration and partial oxygen pressure is well known and the terms may be used interchangeably. The parameters for the patient treatment plan are also obtained (step S302). As shown, these steps may be carried out simultaneously or in any suitable order. The parameters for the patient treatment plan may be accessed from a database which may be stored in any suitable location (remote or local to the computing system) or which may be input by a user. The parameters include the dose 52, energy 54 and pulse geometry 56. The total dose is considered to be delivered in a single pulse and the pulse geometry may be considered to be rectangular with a given height or an instantaneous dose rate and pulse length. The parameters may also include the modality of the therapy, e.g. nature of the particles within the beam, e.g. protons, electrons etc.

The parameters and oxygen concentration are input into the flash effect model (step S304), i.e.

$$F_t(E, p) = \frac{g_4(p) - g_3(p)}{\pi}\left[\arctan\frac{(g_1(p) - E)}{g_2(p)}\right] + g_3(p)$$

and if all of the spectrum of dose depositing charged particles is in a low-LET regimen, the pressure dependence can be reduced to a single version:

$$g(x) = \frac{xa + b}{x + c}$$

where x is the partial oxygen pressure and the parameters, a, b, c, are determined for a single representative energy depending on the case.

The next step is to calculate the damage to the patient as a result of the treatment (step S306). As explained above, the model focuses on the complex damage. The model has two variables: energy and oxygen pressure (which is varying with time). Accordingly, for a single energy of a specific particle, the damage contribution may be calculated per cell, per Gy and per Giga base pair (factoring the length of the DNA strings into the equation) as:

$$M_d = D\int_0^T F_t(E, p(t))dt$$

The damage contribution may be calculated per cell, per Gy and per Giga base pair (factoring the length of the DNA strings into the equation) as:

$$M_d = D\int_0^{Emax}\Psi(E)F_d(P', E)dE$$

The damage may be output as a damage map or matrix $M_d[i,j,k]$ where each point of the map may be known as a voxel. The damage may be output as the number of clusters for which complex damage occurs or may be output as a relative sparing effect where the damage caused by flash radiotherapy is compared to standard radiotherapy. Both examples may be used to quantify the level of damage caused within the irradiated volume to healthy tissue. The second option can be used to quantifying the level of damage to healthy tissue relative to a level of damage caused by radiation which is not flash radiation. The damage data may be output to the user to indicate the effect of the treatment on the patient before the treatment is initiated. The damage information may be used to determine whether the patient will benefit from the tissue sparing effect or not.

The output damage data may then be used to calculate a cost function which is indicative of the cost to the patient of the proposed treatment (step S308). An optimization function is then applied to the cost function to determine which parameters of the treatment plan are adjustable to improve the treatment plan for the patient (step S310). For example, the dose may be optimised to a higher dose. These optimised parameters are then output (step S312). Thus, there is effectively a feedback loop as shown in FIG. 3a above.

Figure 4A:
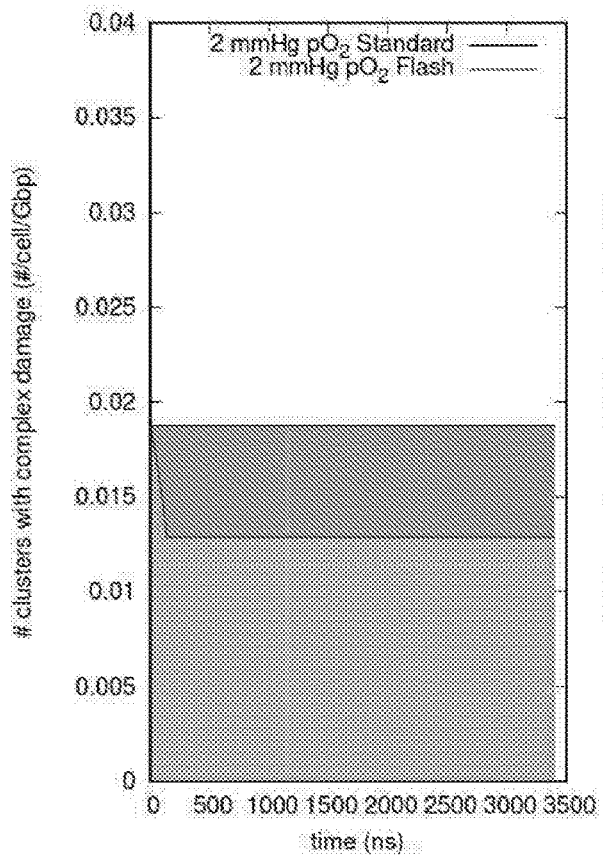
FIGS. 4a and 4b compare the effectiveness over time of standard and flash radiotherapy at different oxygen levels respectively.
Figure 4B:
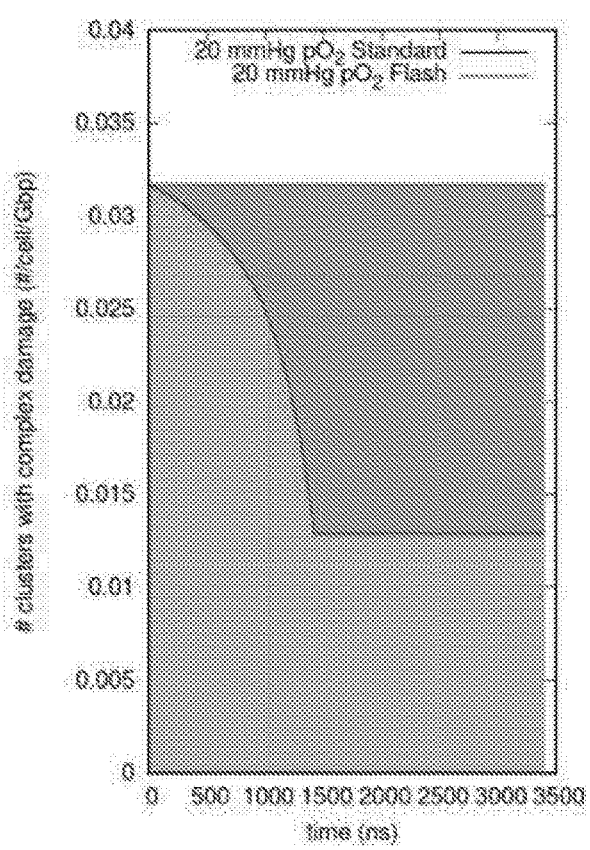

FIGS. 4a and 4b plot the numbers of clusters with complex damage (number of cells/Giga-base pair GBp) against time for standard radiotherapy and flash radiotherapy. The flash radiotherapy is modelled as a standard 3.4 s pulse delivering 15 Gy using the model described above. As a first approximately, a linear inverse ODH is used starting at the initial oxygenation level descending linearly to full hypoxia. The steepest depletion rate of 0.42 mmHg/Gy is used and the instantaneous dose rate is 0.44 cGy/ns. The modality is chosen as an electron beam with a median depositing energy of 2 MeV. Standard radiotherapy is considered to be anything lower than 6 Gy per minute but for comparison, 15 Gy is still the total dose. The generated lesions are per cell, Gbp, and Gy.

FIG. 4a shows the numbers of clusters in a low or moderately hypoxic oxygen environment, e.g. with 2 mmHG $pO_2$ and FIG. 4b shows the number of clusters in a normal oxygen environment, e.g. with 20 mmHG $pO_2$. As shown, the number of clusters with complex damage is constant for the standard radiotherapy at approximately 0.017 per cell per Gbp for the low oxygen environment and 0.032 for the standard oxygen environment. By contrast, the flash radiotherapy initially has the same number of clusters with complex damage but the number of clusters is reduced with time. For the low oxygen environment, the reduction when compared to standard radiotherapy is smaller and decreases linearly initially. For the standard oxygen environment, the decrease is greater and the initial decrease is non-linear. This non-linear effect is due to the co-variance of dose and initial pressure variables. The improvement in performance at higher oxygen levels may be termed the flash effect.

Figure 5A:
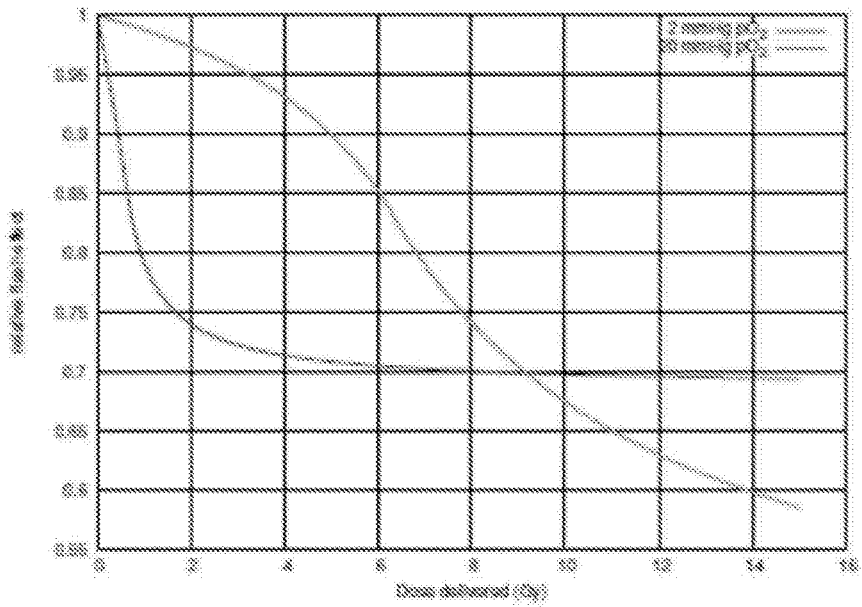
FIG. 5a plots the variation in relative flash effect by dose delivered at two different oxygen levels.
Figure 5B:
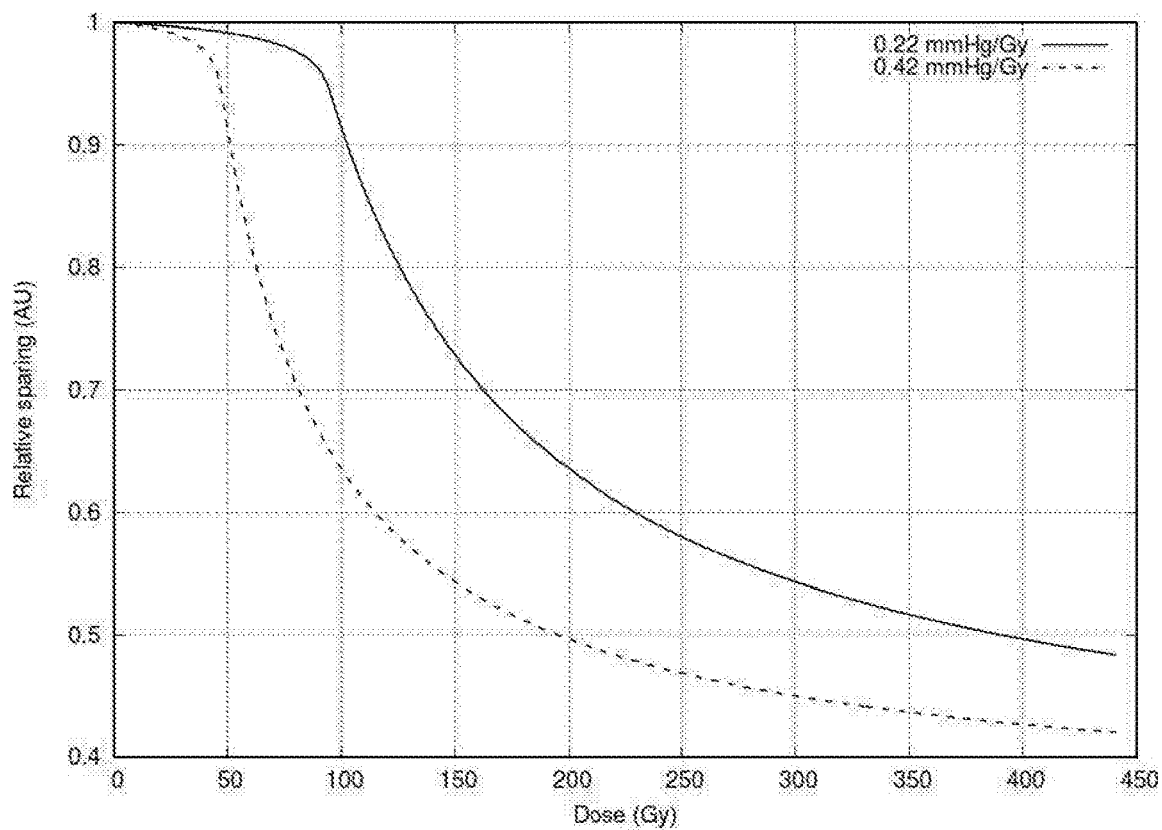
FIG. 5b plots the variation in relative flash effect by dose delivered at two different oxygen depletion rates, for cell cultures in open air (i.e. 20% Oxygen)
Figure 5C:
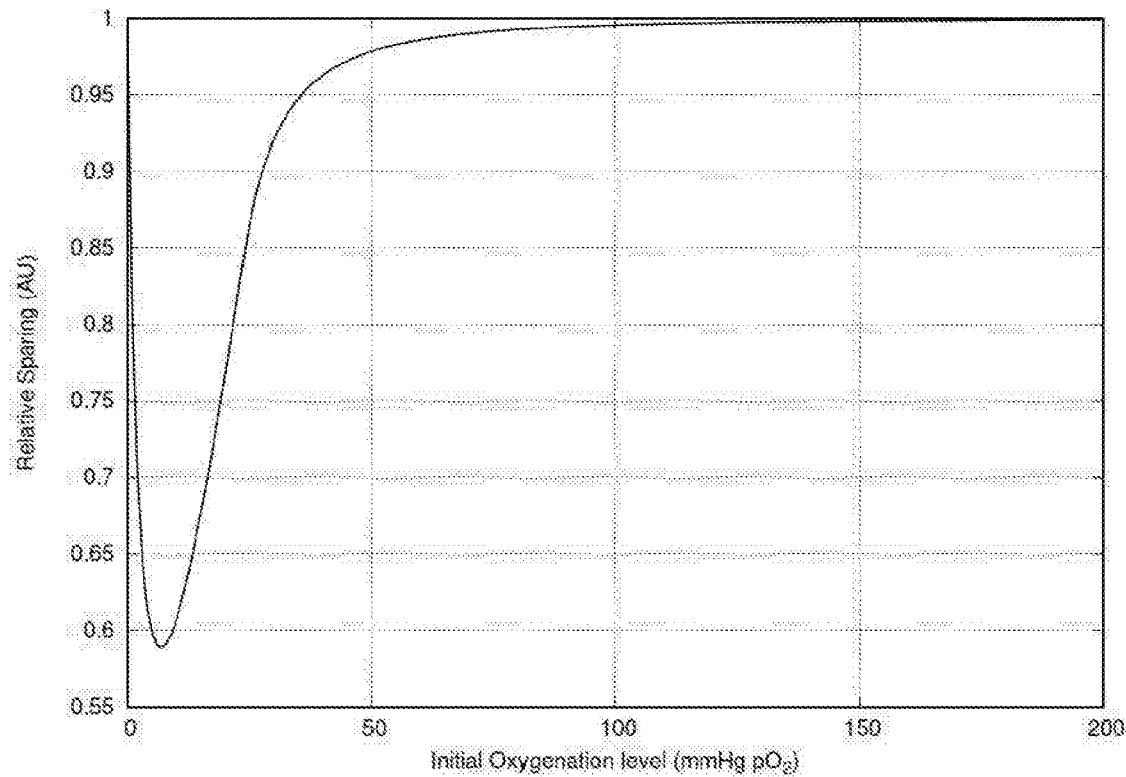
FIG. 5c plots the variation in relative flash effect by initial oxygenation level.

FIGS. 5a to 5c use the model above to explore the flash effect in more detail. FIG. 5a shows the relative flash effect at the two different oxygenation levels of FIGS. 4a and 4b as it changes with dose delivered. The delivered dose is varied by varying the beam on time with the pulse. The relative flash effect compares the flash radiotherapy with standard radiotherapy. One definition of the relative flash effect is the ratio of the number of clusters with cell damage for flash radiotherapy divided by the number of clusters with cell damage for standard radiotherapy. As shown in FIG. 5a, the relative flash effect plateaus quickly at 0.7 for the moderately hypoxic environment and thus there is a dose level of between 2 to 9 Gy where the flash effect is larger for the lower oxygen level. At about 10 Gy, there is a cross over and the well oxygenated tissue exhibits a larger amount of sparing.

For some treatments, the initial oxygenation level may not always be determined accurately. Moreover, for some treatments, it is reasonable to assume an atmospheric oxygenation level, which in normal circumstances is about 20% availability of oxygen in air, i.e. the treatment takes place in a well oxygenated environment. FIG. 5b plots the variation in relative flash effect with dose for two different oxygen depletion rates R of 0.22 mmHg/Gy and 0.42 mmHg/Gy. Again relative flash effect is the effect of the flash radiation when compared to standard radiation. In both cases, the oxygen conditions are comparable to atmospheric conditions and different doses are delivered in 3.4 μs. The flash effect is normalised to (i.e. relative to) the same conditions, e.g. same dose, time and atmospheric conditions but no oxygen depletion occurs. In these cases, extremely high doses, e.g. above 75 Gy, are required to exhibit the flash effect.

The initial oxygenation level (i.e. the oxygenation level at the beginning of the pulse) appears to be critical. FIG. 5c shows the dependency of the relative flash effect on the initial oxygenation level again using the 3.4 μs pulse delivering 15 Gy. It is clear that in some cases, small variations in oxygenation can have a major impact on the sparing effect. Again relative flash effect is the relative effect of the flash radiation when compared to standard radiation. FIG. 5c also shows that the oxygenation level by itself is already degenerate.

Figure 6A:
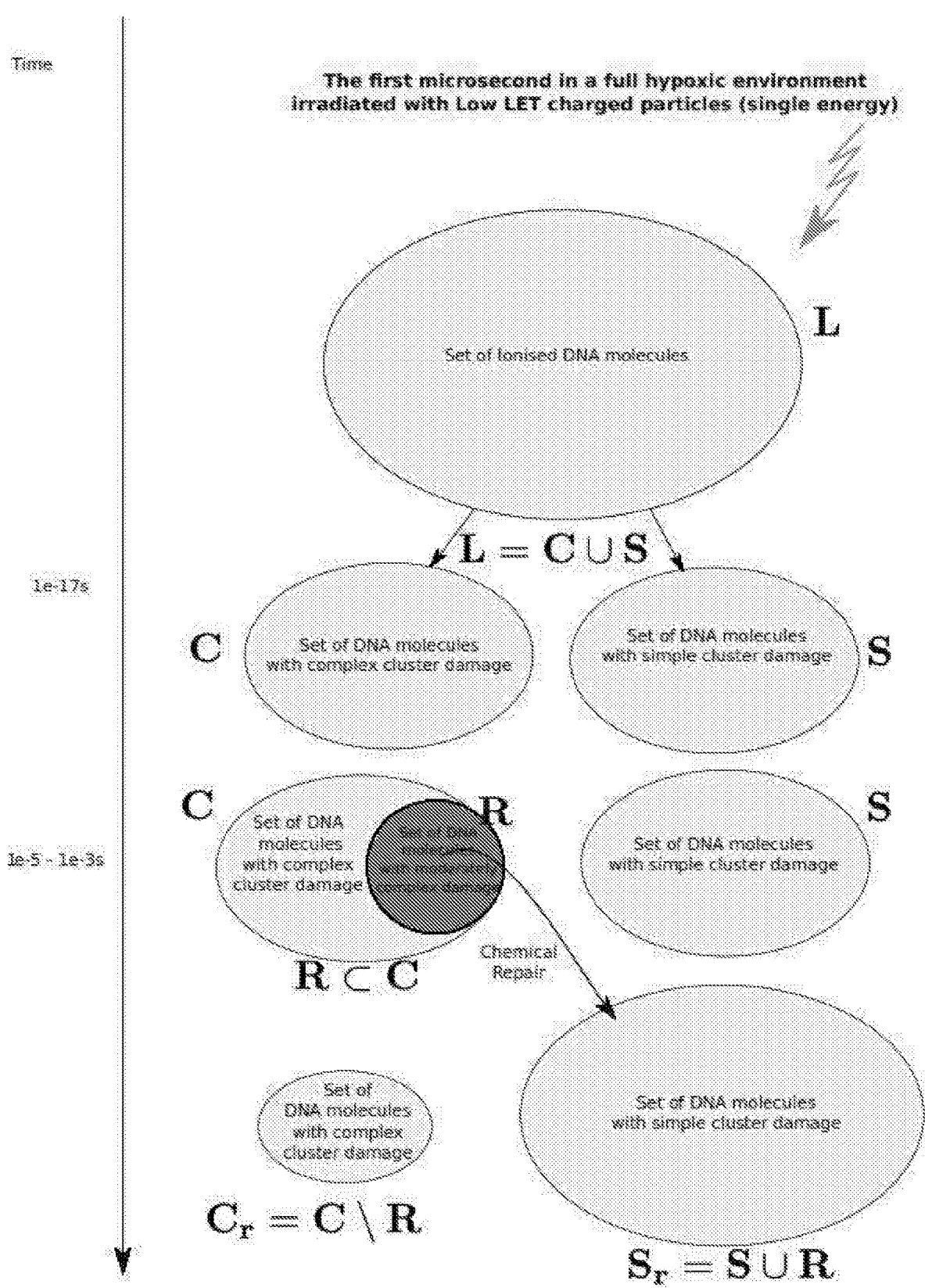
FIGS. 6a and 6b are set theory representations of oxygen effects in full hypoxic and oxygenated environments respectively.
Figure 6B:
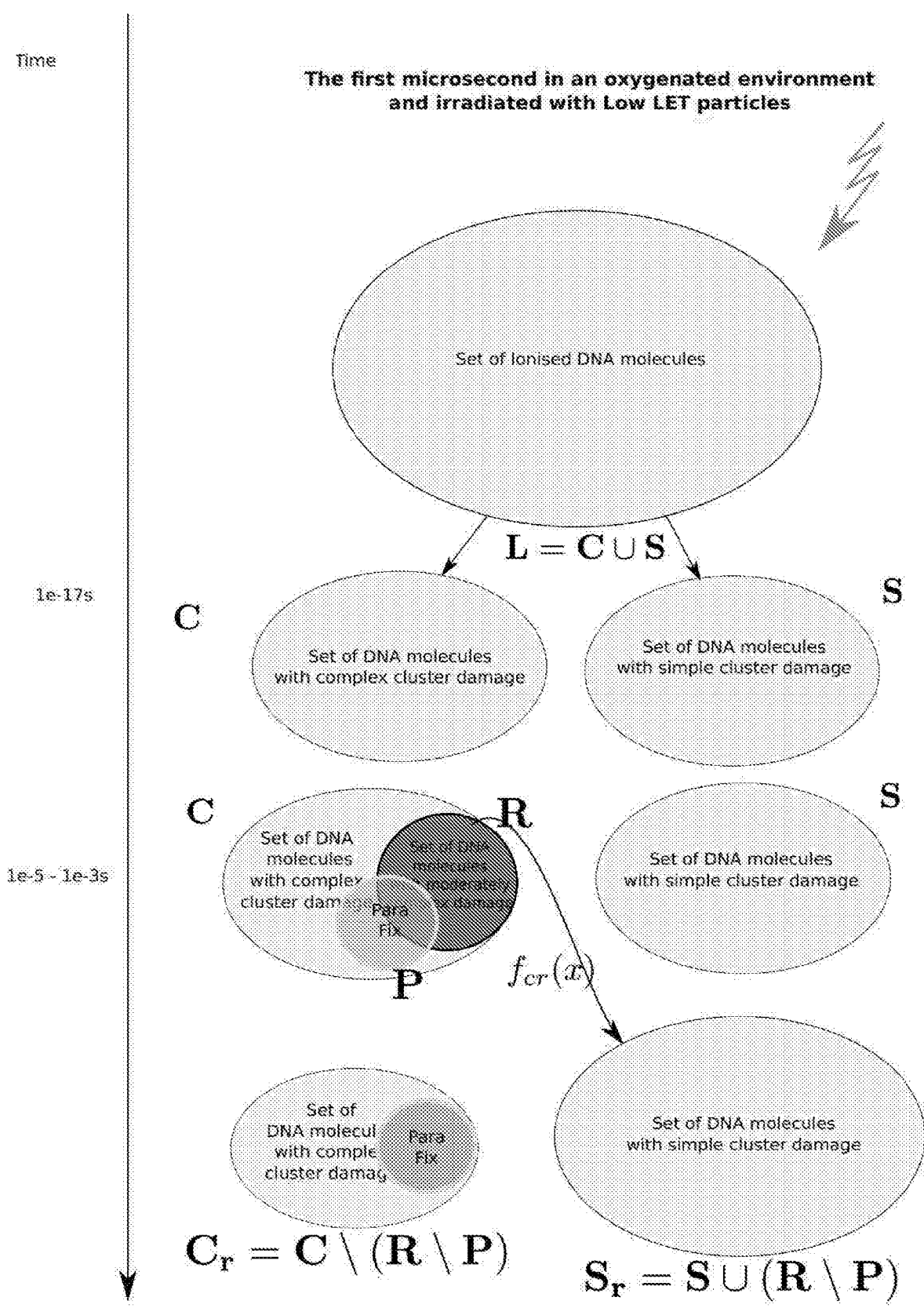

The following passages describe the components of the flash effect model. As summarised above, the flash effect model incorporates a relationship quantifying the oxygenation effect on DNA-damage based on the oxygen fixation mechanism that is in competition with chemical repair. FIGS. 6a and 6b illustrate how this relationship may be expressed using a set theory model. FIG. 6a illustrates a schematic overview of the process of chemical repair without the availability of oxygen, i.e. in a system with complete hypoxia, and thus only considers chemical repair. FIG. 6b illustrates a schematic overview of the process of chemical repair with oxygen present.

In both cases, the dose is delivered by charged particles. When irradiating cells with ionising radiation, DNA damage is generated through direct and indirect damage events. These damage lesions (or regions of damaged tissue) are then subject to chemical repair in the first few microseconds and in a longer time frame are subject to biological repair mechanisms. Typically, models of cell death and apoptosis distinguish between simple and complex damage. Simple DNA-damage lesions include single strand breaks (SSR), single base damage (SBD), dual SSB with a spatial distance larger than a single turn of the α-helix (2SSB). Anything more complex than that is considered to be complex damage (which is denoted by DSB). It is widely assumed that the latter type of damage is closely related to cell death.

The set of all DNA-damage lesions in a cell due to a dose of 1 Gy in a cell over a length of 1 Giga-base pair (Gbp) is denoted by L. A subset C of the set L has lesions which are categorised as complex and a subset S of the set L has lesions which are categorised as simple. A subset R of the set C of complex lesions are repairable. A function $f_{cr}$ from C to S is used to model chemical repair. The function only works on lesions that can be repaired and thus defines its own domain R. Two further sets are defined, namely $S_R$ which is the set of simple lesions after chemical repair and $C_R$ which is the set of complex lesions after chemical repair.

FIGS. 6a and 6b illustrate relationships between the sets using standard set theory symbolism in which U denotes the union of two set, ∩ denotes the intersection between two sets, \ denotes the subtraction of one set from another (i.e. it removes the common elements from the first set) and R⊂C indicates that set R is a subset of set C. Finally, the symbol #denotes the cardinal number of a set (i.e. the number of elements in the set).

FIG. 6a shows the repair process without oxygen. This reduces the number of damage clusters which can be classified as complex damage. The only clusters which are not reduced are already so complex that chemical repair does not affect their status. We formalise this train of thought in terms of naïve set theory (i.e. no sets are considered which have an infinite number of elements). This allows us to treat this chemical repair process as a statistical system. This is another important assumption or restriction which is incorporated into the model and means that oxygen depletion is a statistical process and is not modelled as a localised phenomenon.

As shown in FIG. 6a, the set of complex lesions is reduced by the chemical repair process and after applying the defined function, we obtain $f_{cr}(C)=C\backslash R$. The number of complex lesions left for the biological process to repair is thus $\#C_R = \#C - \#R$. This is equivalent to the term $M_0$ in classical formalism. Similarly, the set of simple lesions is changed and its size is increasing. In this case, $f_{cr}(C)=S \cup R$.

In other words, the function $f_{cr}$ applied on the domain R is an injection in $S_R$. By categorising the repair process as represented by the function $f_{cr}$ as an injection over R, we are making the assumption that all repairable lesions are indeed repaired or that the compounds needed for the repair are not a scarce resource.

FIG. 6b illustrates how oxygen may be introduced into the model by using the oxygen fixation mechanism. This process fixed lesions by binding the very reactive oxygen molecules, for example as described in "Effects of radiation quality and oxygen on clustered DNA lesions and cell death" by Stewart et al published in Radiation research in 2011; 176(5):587-602. For FIG. 6b, another set P which is a subset of C is defined as the set of lesions that have been fixated by the available oxygen. There is a subset of lesions which are repairable lesions which are fixated and this is the set defined by the intersection R ∩ P. These lesions are not subject to the chemical repair process anymore. The process of chemical repair in the presence of oxygen may be formalised in mathematical terms as an injection denoted by $f_{cr}(x)$ with $x \in R\backslash(R \cap P)$ or $$R\backslash(R \cap P) \xrightarrow{f_{cr}} S_R$$

In other words, only elements of the set of repairable lesions that do not belong to the fixated lesions are eligible for chemical repair. The resulting lesions are classified as belonging to the set of simple lesions, which is now denoted as $S_R$. Conversely, the resulting set of complex lesions $C_R$ is changed accordingly because rather than the total set R being subtracted, the set R\P is subtracted. The biological repair process is thus presented with the following number of complex lesions in need of biological repair: $\#C_R = \#C - \#(R\backslash P)$ If there is no oxygen, then #P=0 and $\#C_R$ is minimised. In the presence of oxygen, we assume that the original number of chemical repairable lesions does not change for the same modality (and energy). Thus, the only changeable element is the number of fixated lesions which is distributed throughout the lesions with specific preference, making the ratio constant for a given modality and energy. The increase of available complex lesions in need of repair is proportional to #P or more formally:

$$\#C_R = \#(C\backslash R) + a \cdot \#(P)$$

This implies that we need to estimate the relative number of chemically repairable lesions which are fixated. This is a ratio of the total number of fixated lesions which is given by #P.

In this model, we are agnostic about the specific mechanism of oxygen fixation apart from the facts that oxygen binding takes place and that oxygen is a scarce resource. Such a mechanism may be described by a typical pharmacological differential equation which has been generalised as a saturation behaviour in "Saturation behaviour: a general relationship described by a simple second-order differential equation" by Kepner et al published in Theoretical biology and medical modelling 2010; 7:11-11. Accordingly, the solution for #P may be expressed as a two-parameter rational function of the form:

$$\# P = \frac{x}{q_1 x + q_2}$$

where x is a universal variable representing the scarce resource, in this case a good candidate is the partial oxygen pressure [pO$_2$] and 1/q$_1$ denotes the saturation level and 1/q$_2$ the initial slope.

The expression for #P can be transformed linearly to reflect the amount of chemically repairable damage clusters and the equation #C$_R$=#(C\R)+a·#(P) may be rewritten using a, b ∈ Real Numbers as:

$$a\frac{x}{q_1+q_2 x}+b \text{ or } \frac{ax}{q_1 x+q_2}+\frac{b(q_1 x+q_2)}{q_1 x+q_2}$$

This equation can then be reduced to three parameters by dividing both the numerator and denominator by q$_2$ to give:

$$\frac{x(C_1+C_2)}{x+C_3} \text{ with } C_1=\frac{a}{q_2}+b, C_2=b\frac{q_1}{q_2}, C_3=\frac{q_1}{q_2}$$

It is noted that if full hypoxia rather than the normoxic environment is considered as the reference condition, the arrangement above leads back to the empirical model for the oxygen fixation hypothesis proposed in "Effects of radiation quality and oxygen on clustered DNA lesions and cell death" by Stewart et al published in Radiat Res 176, 587-602 in 2011:

$$pR(y,[O_2])=1-\frac{[O_2]+K}{[O_2]+M(y)K}$$

where [O$_2$] denotes the oxygen concentration in %, the parameter K is the oxygen concentration at which half the maximum of possible repaired DNA radicals are removed, and M(y) is a function of y=(z$_{eff}$/β)$^2$, the square of the ratio of effective charge of the particle to its speed in units of the speed of light (c). The Stewart paper suggests an empirical model for the oxygen fixation hypothesis which could be used as an alternative to the set theory model described above. A similar empirical model is described in "A mechanistic investigation of the oxygen fixation hypothesis and oxygen enhancement ratio" by Grimes et al published in Biomedical physics and engineering express 2015; 1(4) for estimating the fraction of chemically repaired DNA radicals p$_R$(y,[O$_2$]). The model here could also be incorporated as an alternative to the set theory model but as shown above the set theory model is a useful way to express the oxygen fixation mechanism.

The model depends on the pulse geometry, pulse length instantaneous dose rate (i.e. Gy/ns), total dose delivered in a single pulse and initial oxygen level in a voxel (point in 3D space).

The energy dependence of oxygen effects is then considered to further develop the model. In other words, the relationship quantifying the oxygen effect on DNA-damage is then used in a model describing the dose dependent oxygen depletion within an ultra-high dose pulse. "A closed parametrization of DNA-damage by charged particles, as a function of energy—a geometrical approach" by Van den Heuvel et al published in PLoS ONE 2014, 9(10) describes how the behaviour of generating complex damage may be expressed as a function of a charged particle. As set out above, complex damage is any damage more complex than a double strand break. For convenience, the notation DSB is used for complex damage. In the paper by Van den Heuvel, the amount of complex damage as a function of the kinetic energy E of a given particle modality can be expressed as:

$$DSB=\frac{dsb_0-dsb_\infty}{\pi}\left[\arctan\left(\frac{E_0-E}{\Gamma}\right)\right]+dsb_\infty$$

Where E$_0$ is the energy at which half the particles interact in a high LET fashion (i.e. generating complex damage by interaction of a single particle with an irradiated volume (e.g. the target)), Γ is the width of the transition, the terms dsb$_0$ and dsb$_\infty$ do not necessarily have a physical meaning but represent the values of the inverse tangent limits. However, it is clear that dsb$_0$ and dsb$_\infty$ are closely related to #C$_R$.

The expression below is valid for all levels of available damage cluster but needs to be adapted to the relative amount of damage for which these processes (i.e. chemical repair and oxygen fixation) can be applied:

$$\frac{x(C_1+C_2)}{x+C_3}$$

In other words, it is scaled with #R\(R ∩ P) relative to the total number of complex lesions (#C). In the case of high-LET charged particle interactions we observe that #C is a lot larger than #R\(R ∩ P), making any contribution of an oxygenation effect negligible. This is due to two mechanisms. Firstly, the relative reduction of repairable lesions:

(#R/#C)↓

Secondly, the relative decrease of available oxygen as it is used up by increased numbers of already irreparable lesions.

$$\frac{\#P}{\#(C\backslash R)}\downarrow$$

Without loss of generality, it can be assumed that energy and pressure are in no way correlated. This implies that the dependence on oxygen pressure is only expressed in the parameters dsb$_0$, dsb$_\infty$, E$_0$ and Γ in the equation above. For a single energy and particle both the formulas in the preceding paragraphs can be applied sequentially. In the case of poly-energetic environments they need to be applied for every energy separately. Alternatively, they can be combined. A good possibility for combining the dependence of damage on energy and oxygen pressure could be the following expression:

$$F_t(E,p)=\frac{g_4(p)-g_3(p)}{\pi}\left[\arctan\frac{(g_1(p)-E)}{g_2(p)}\right]+g_3(p)$$

with $$g_i(x)=\frac{xa_i+b_i}{x+c_i} \text{ for } i\in\{1,2,3,4\}$$

Figure 7A:
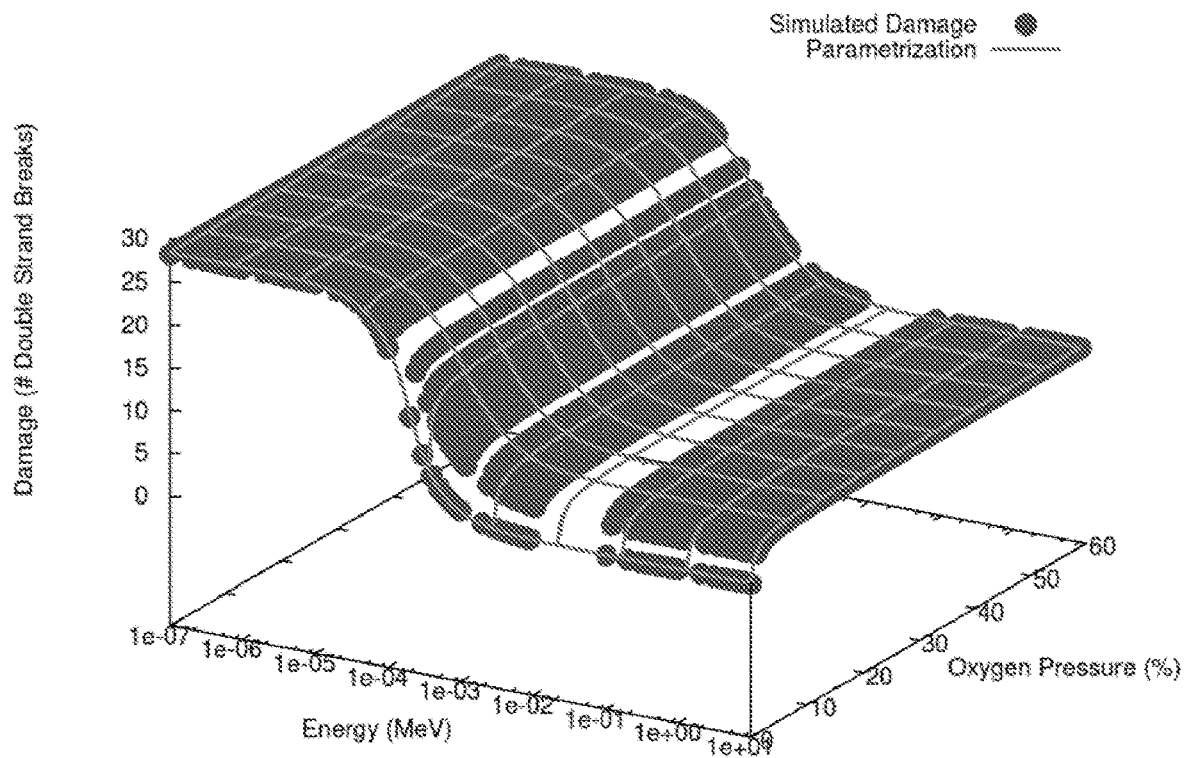
FIGS. 7a to 7d are output representations of the variation in damage with energy and oxygen pressure for four different types of radiation: electrons, protons, alpha-particles and carbon ions.
Figure 7B:
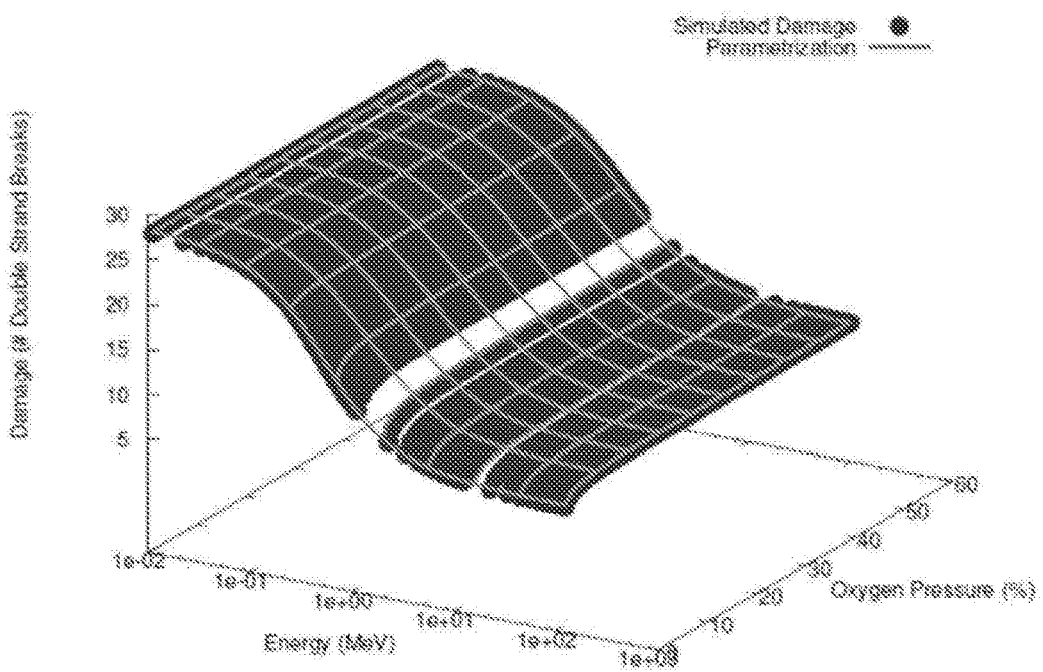
Figure 7C:
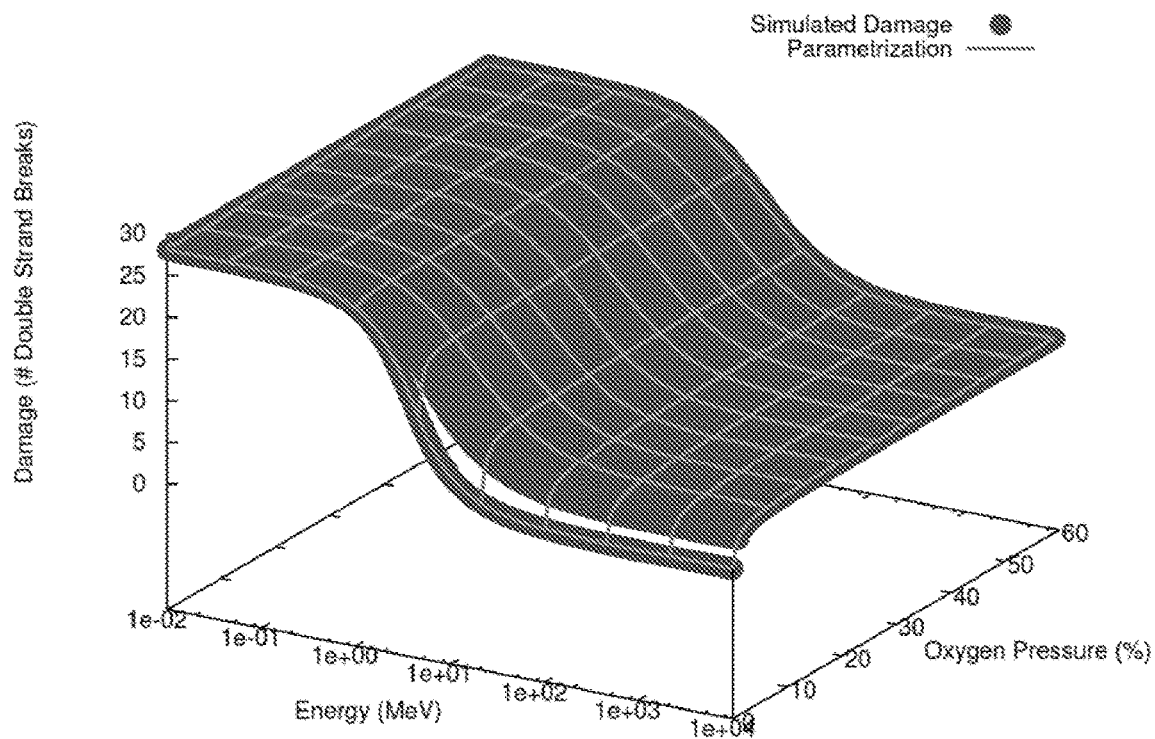
Figure 7D:
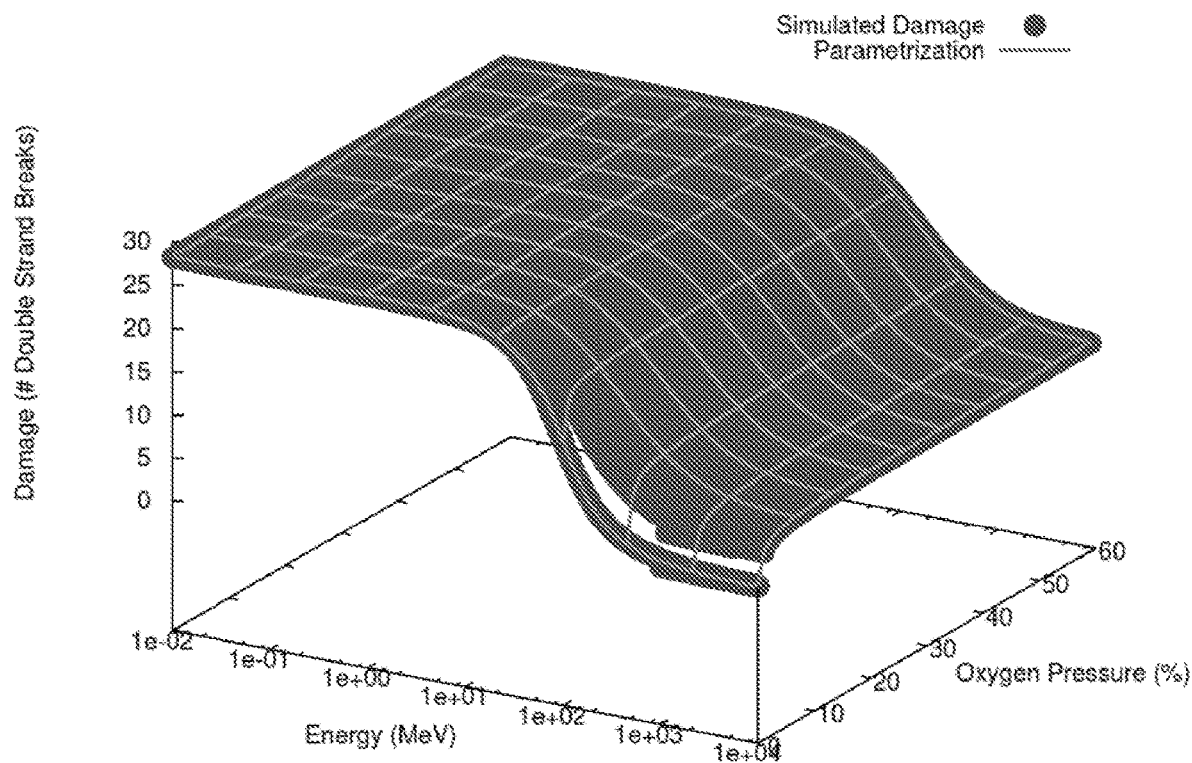
Figure 8A:
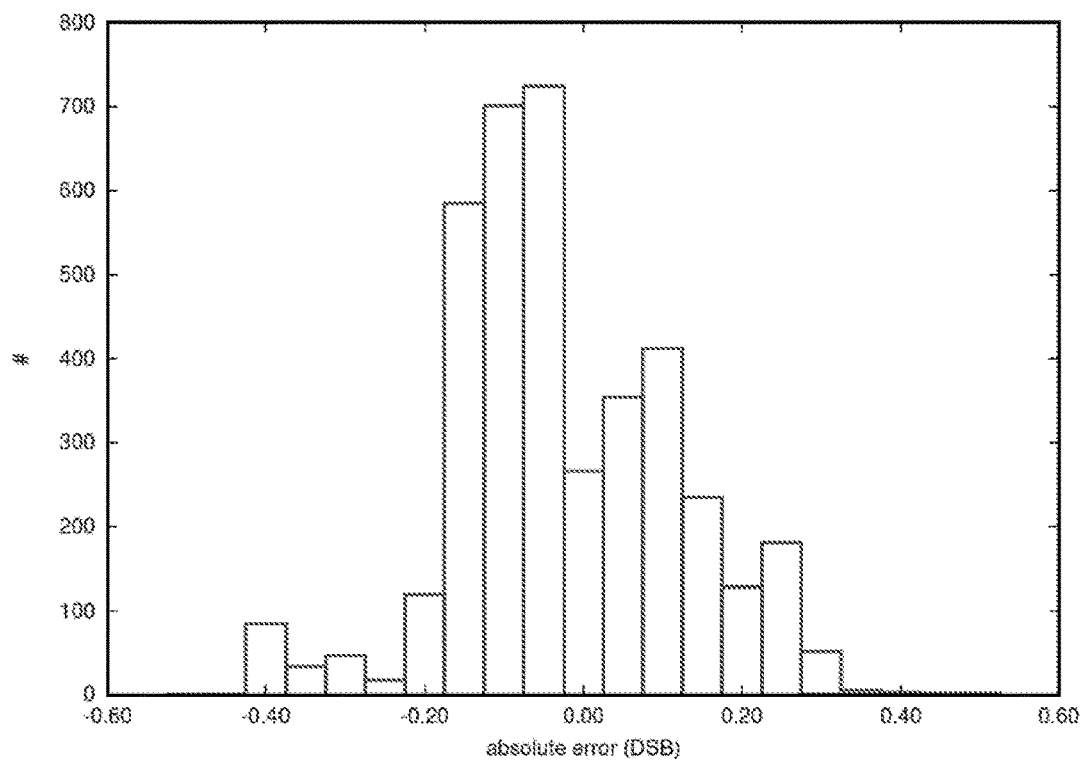
FIGS. 8a to 8d are histograms of the absolute error of the results in FIGS. 7a to 7d when compared to a different model.
Figure 8B:
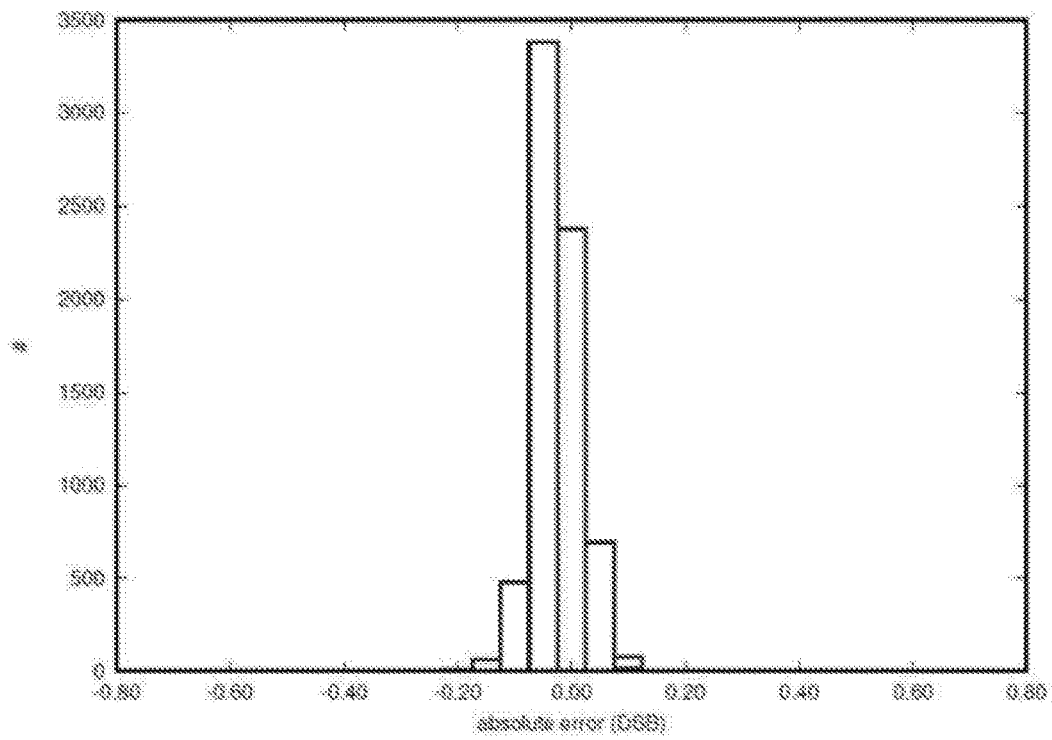
Figure 8C:
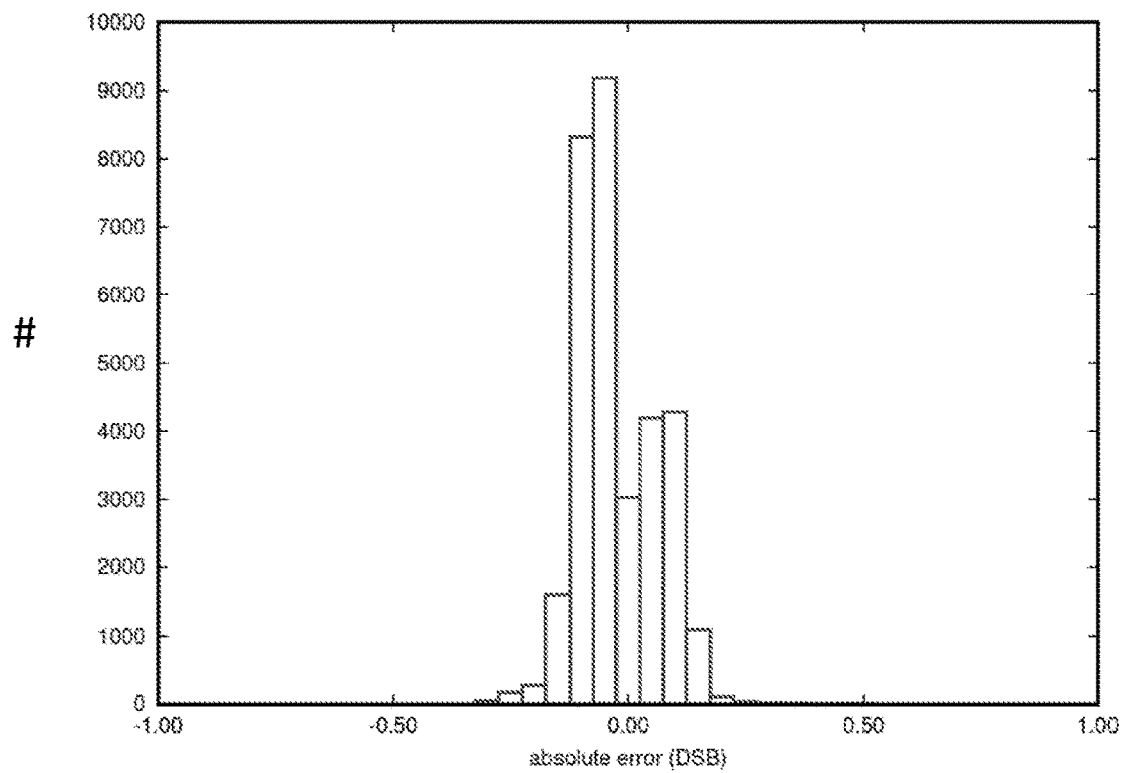
Figure 8D:
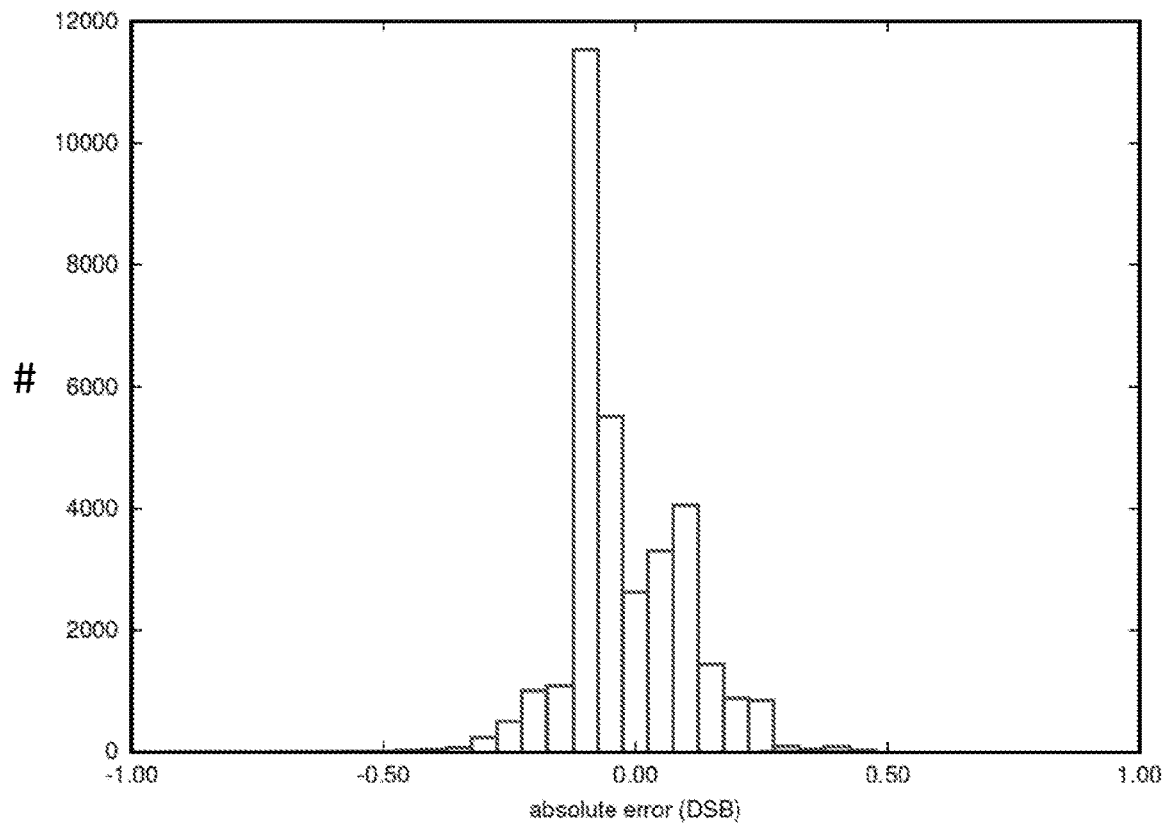

FIGS. 7a to 7d illustrate example outputs from the flash-effect model which may be used to calculate the damage maps. FIGS. 7a to 7d show the variation in the number of lesions having complex damage as functions of energy (MeV) and Oxygen pressure (%). FIG. 7a models an electron beam, FIG. 7b models a proton beam, FIG. 7c models a beam of α-particles and FIG. 7d models a beam of carbon ions. The kinetic energy range is chosen on a logarithmic scale and is such that both the high and low LET energy spectra are adequately covered for each type of beam. The oxygen levels vary between 0% and 60%.

The model is validated by comparing with the Monte Carlo simulations described above. MCDS Version 3.10 was used with the following parameters: a DNA length of 1 Gbp (giga base pairs) and a nucleus diameter of 5 m. In the MCDS algorithm, the geometry of the DNA molecule is not a specific parameter. Four parameters are used: the DNA segment length which is an ad-hoc parameter expressed as base pairs, the number of strand breaks generated, the number of base pair damages generated by the defining and a parameter (bp) describing the minimal separation between damage locations for damage not to be counted as being in the same cluster. Other variable input parameters were the modality (i.e. type of energy depositing parameter), the energy in MeV and the oxygen concentration in %.

FIGS. 8a to 8d are histograms showing the distribution of relative errors between the results of flash effect models as shown in FIGS. 7a to 7d and similar results generated by the MCDS algorithm. The table below summarizes the statistics of the residual errors. As shown in the table and FIGS. 8a to 8d, values of number of complex lesions range between 5 and 30 expressed per cell, per Giga base pair, and per Gy. Most outliers are found in the energy range in which the transition of low to high LET regimen occurs. The standard deviation of the order of 1% shows that there is good agreement between the two models.

| Modality | Energy range (MeV) | Standard deviation | Range |
|---|---|---|---|
| Electron | 1e−07-10 | 0.16 | [−1.18 1.18] |
| Proton | 0.01-1000 | 0.21 | [−0.52 1.37] |
| Alpha particle | 0.01-10000 | 0.08 | [−0.28 0.56] |
| Carbon ($C^{6+}$) | " | 0.13 | [−1.12 0.52] |

Further validation of the flash effect model has been done by recreating a pre-clinical treatment described in "Irradiation in a flash: Unique sparing of memory in mice after whole brain irradiation with dose rates above 100 Gy/s" by Montay-Gruel et al published in Radiotherapy Oncol 124, 265-360 in 2017. In this paper, the authors subjected a cohort of mice to brain irradiations with different dose rates and tested the mental capacities by estimating the recognition ratio (RR) in an object recognition test. Quoting from the paper we have "evaluation of the recognition ratio (RR) two months post irradiation [was performed] for groups of mice that received sham irradiation (control) and 10 Gy (whole beam irradiation) with a dose rate of 0.1, 1.0, 3, 10, 20, 30, 60, 100, or 500 Gy/s, or with a single 1.8 μs electron pulse (1 Pulse)".

In recreating the experiment, it is assumed that full re-oxygenation occurs between pulses and this is reasonable because the time between pulses is of the order of 10 ms. Accordingly, only the dose within a single pulse is of interest. This is a reasonable assumption because the original cell-based experiments shows that the effect was not present when delivering the treatments in 2 pulses 2.5 ms apart. In the ODH formalism, this is the special case where the ODHs of all pulses are identical. Thus, it is also assumed that each pulse is identical in height and length. In order to apply the flash effect model, we need to convert from the Gy/s notation to a more refined cGy/ns within a single pulse as follows:

1) Divide the Gy/s expression by the pulse repetition frequency to get the dose per pulse (DPP):

$$\frac{xGy/s}{100}$$

2) Calculate the relative sparing effect using given depletion rates and initial oxygenation rates which should be of the order of 20 mmHg $pO_2$ for healthy tissue or lower.

The model described above is then applied using a depletion rate of 0.42 mmHg $pO_2$/Gy and an initial oxygenation level of 3 mmHg $pO_2$. The results are plotted in FIG. 9a which shows on the left axis the recognition rates as a function of dose rate determined by the paper and on the right axis the inverse of the flash effect ratio. A clear correlation is shown. This is calculated using the Spearman Ranking as ρ=0.881 which even with the limited number of points (10) is significant at p<0.01.

Figure 9A:
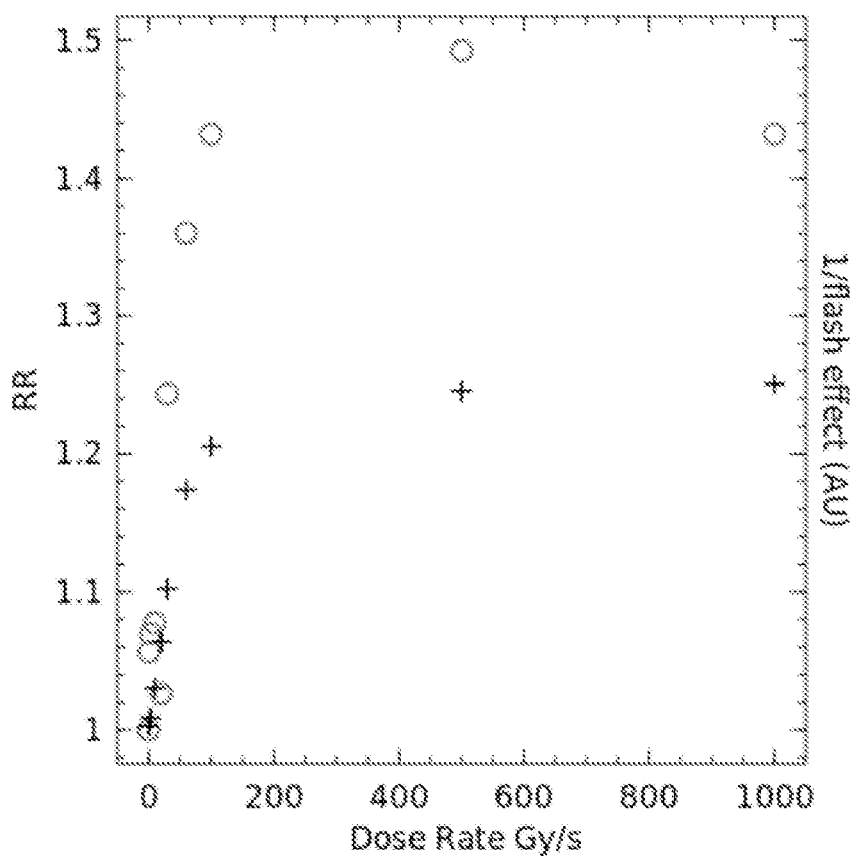
FIGS. 9a and 9b compare the results of an experiment with the modelled results predicted by the system of FIG. 1.
Figure 9B:
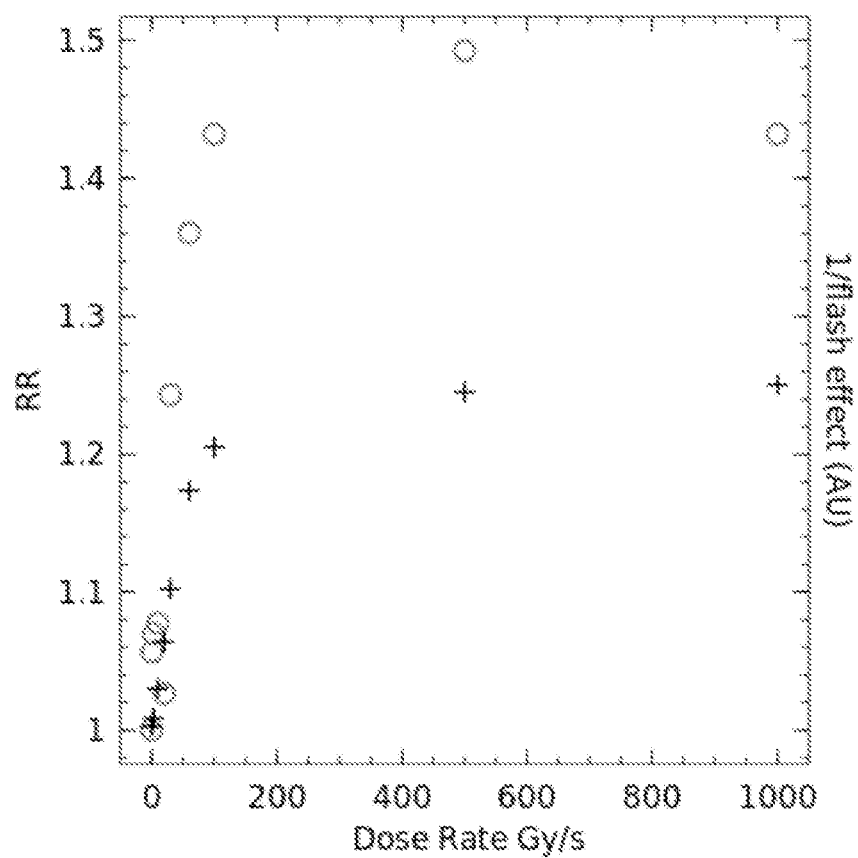

The model is also applied using a depletion rate of 14.0 Torr $pO_2$/Gy and an initial oxygenation level of 4 Torr $pO_2$. The results are plotted in FIG. 9b. A clear correlation is shown. This is calculated using the Spearman Ranking as p=0.881 which even with the limited number of points (10) is significant at p<0.01. The latter correlates with a critical Spearman Ranking correlation coefficient $ρ_c$=0.794 as provided by "Significance testing of the spearman rank correlation coefficient" by Zar et al published in J. Am. Stat. Assoc. 67, 578-580 in 1972. As shown by FIGS. 9a and 9b, the correlation is robust for a range of oxygen depletion rates and initial oxygenation levels. In FIGS. 9a and 9b, the open circles are recognition rates as a function of dose rate and the plus signs are the inverse of the FLASH effect ratio.

The model which is described in the application thus has good correlation with experimental results and also an earlier model. The model may be considered to combine an oxygenation fixation mechanism, an oxygen depletion model and a relationship between the energy dependence of oxygen effects and damage.

The work described above provides some interesting corollaries which impact the applicability of flash therapy on clinical practice. These may include that the level of initial oxygenation in a given tissue is critical to the magnitude of the flash effect. Furthermore, there is a dose dependency of the flash effect. If the dose is too low, no flash effect exists. Mathematically, the flash effect is considered degenerate in its modelling parameters. This means that a single result can be obtained by different combination of specific parameters (oxygenation level, dose rate, total dose delivered). In addition, oxygenation level by itself is already degenerate.

The existence of a threshold dose for the flash effect may restrict its applicability and may also make the physical implementation difficult, e.g. when using scanned proton beams or when combining beams from different angles. In addition, the lower limit to the flash effect still exhibits a biological effect commensurate with about 50% of the original dose. This combined with the threshold dose means that tissue which we want to spare, will still receive a significant effective dose. The dependency on the initial oxygenation is another major issue because it is difficult to measure in a clinical situation. Moreover, the dependency may be quite steep at some levels, giving rise to major uncertainties. Accordingly, it may be preferred to use a methodology which is able to accurately measure the oxygenation levels in-vivo.

As explained above, there are some assumptions with respect to the oxygen depletion and fixation process. The first is that oxygen depletion is a statistical process and is not modelled as a localised phenomenon related to damage induction. In other words, the induction of DNA-damage is not coupled to the oxygen depletion. However, given the discrepancy in oxygen depletion rates published in the articles by Town and Whilliams, it is still necessary to consider flash effects on oxygenation as a localised phenomenon giving rise to pockets of relative hypoxia. Secondly, the impact of oxygen on the DNA-damage induction is a microscopic process whereby oxygen is used up in a very small volume with a diameter of a few nanometres.

The results above only consider electrons and photons. However, the results can be readily expanded to other modalities like protons, alpha-particles and carbon ions. Indeed the mathematical damage model shows that the same approach for different particles is valid and mathematically similar, but a different energy levels, and the oxygenation model is identical. However, the simplification that is used above in relation to the oxygenation characteristics from a single energy is no longer valid. In those cases, part of the energy deposition now occurs in the steep region of the curves shown in FIG. 5b. However, this can be resolved using a weighted sum of the spectral contributions to the damage. Together with the oxygen impact model, one can calculate the impact of spectral composition for each type of particle. A short calculation shows that for protons the single energy approximation is still reasonable, while for a particles this is not the case. Finally, in the case of carbon ions, the oxygen effect is negligible in the SOBP and this model predicts a lack of flash effect in this modality. However, it is not clear whether the oxygen depletion model in other modalities or even have different characteristics.

It is also noted that the above approach is a physico-chemical process rather than a biological process.

At least some of the example embodiments described herein may be constructed, partially or wholly, using dedicated special-purpose hardware. Terms such as 'component', 'module' or 'unit' used herein may include, but are not limited to, a hardware device, such as circuitry in the form of discrete or integrated components, a Field Programmable Gate Array (FPGA) or Application Specific Integrated Circuit (ASIC), which performs certain tasks or provides the associated functionality. As illustrated, the described elements may be configured to reside on a tangible, persistent, addressable storage medium and may be configured to execute on one or more processors. These functional elements may in some embodiments include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. Although the example embodiments have been described with reference to the components, modules and units discussed herein, such functional elements may be combined into fewer elements or separated into additional elements. Various combinations of optional features have been described herein, and it will be appreciated that described features may be combined in any suitable combination. In particular, the features of any one example embodiment may be combined with features of any other embodiment, as appropriate, except where such combinations are mutually exclusive.

Throughout this specification, the term "comprising" or "comprises" means including the component(s) specified but not to the exclusion of the presence of others. Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A computer system for analysing a radiation treatment plan using a dose of flash radiation to irradiate a volume within a patient, the computer system comprising
   a processor which is configured to
   obtain oxygen pressure information for the volume to be irradiated;
   obtain parameters from a patient treatment plan;
   input the obtained oxygen pressure information and parameters in to a model which predicts complex damage within the irradiated volume caused by the dose of flash radiation;
   output a prediction, using the model, of the complex damage caused within the volume by the dose of flash radiation; and
   quantify, using the prediction, a level of damage to healthy tissue within the irradiated volume;
   wherein complex damage is damage which is more complex than a double strand break within DNA in patient tissue and
   wherein the model is a function of energy of particles within the radiation and oxygen pressure which varies with time.

2. The computer system of claim 1, wherein the processor is further configured to
   quantify the level of damage to healthy tissue relative to a level of damage caused by radiation which is not flash radiation and
   determine whether the dose of flash radiation would produce a sparing effect.

3. The computer system of claim 2, wherein the processor determines that the treatment plan does not produce a sparing effect, the processor is further configured to
   adjust at least one of the parameters obtained from the patient treatment plan and
   output the at least one adjusted parameters.

4. The computer system of claim 3, wherein the processor is further configured to adjust at least one of the parameters by:

calculating a cost function based on the predicted complex damage; and applying an optimisation function to the calculated cost function to determine optimised parameters including at least one adjusted parameter.

5. The computer system of claim 1, wherein the processor is configured to output the prediction of complex damage in the form of a three-dimensional damage map $M_d[i,j,k]$.

6. The computer system of claim 5, wherein the processor is configured to predict complex damage caused by every single charged particle in each cell within the damage map by integrating the model over the energy spectrum.

7. The computer system of claim 6, wherein the processor is configured to predict complex damage for each cell using:

$$M_d = D \int_0^{E_{max}} \Psi(E) F_d(P', E) dE$$

where D is a three-dimensional matrix of dose, $\Psi(E)$ is a dose depositing charged particle field and $P'=T(P)$ where P is a three-dimensional matrix of oxygen pressure information and T is a mapping which transforms spatial coordinates of P to match D.

8. The computer system of claim 5, wherein the processor is configured to predict complex damage due to varying oxygen pressure in each cell within the damage map by integrating the model over time.

9. The computer system of claim 8, wherein the processor is configured to predict complex damage for each cell using:

$$M_d = \int_0^T F_t(E, p(t)) dt$$

where $M_d$ is the damage map, $F_t$ is the model, E is energy and p(t) is the variation of oxygen pressure with time.

10. The computer system of claim 1, in which the model is expressed as:

$$F_t(E, p) = \frac{g_4(p) - g_3(p)}{\pi} \left[ \arctan \frac{(g_1(p) - E)}{g_2(p)} \right] + g_3(p)$$

with $$g_i(x) = \frac{x a_i + b_i}{x + c_i} \text{ for } i \in \{1, 2, 3, 4\}$$

where

E is energy p is oxygen pressure x is a universal variable which represents oxygen, $a_i$, $b_i$ and $c_i$ are real numbers determined by the type of flash radiation.

11. The computer system of claim 1, wherein the model quantifies damage due to oxygenation effects with an oxygen fixation mechanism which is expressed using set theory in which there is a set L of damaged regions within the patient tissues, within the set L there is a subset C of damaged regions which are classified as complex and within the subset C, there is a subset P of complex damaged regions which are fixated by oxygen, a subset R of complex damaged regions which are repairable by chemical repair and a subset $C_R$ of complex damaged regions which remain to be repaired by biological repair.

12. The computer system of claim 11, wherein the number of complex damaged regions within the subset $C_R$ is proportional to the number of damaged regions within the subset P.

13. The computer system of claim 11, wherein the oxygen fixation mechanism determines the number of damaged regions within the subset P using a differential equation which defines saturation behaviour.

14. The computer system of claim 13, wherein the relationship between $C_R$ and P is transformed linearly to reduce the number of variables to three parameters by multiplying by the initial slope of the differential equation.

15. The computer system of claim 1, wherein the parameters include modality of the flash radiation, magnitude of the dose, energy of the dose and pulse geometry of the dose.

16. The computer system of claim 15, wherein the modality of the flash radiation is selected from electrons, photons, α particles and carbon particles.

17. The computer system of claim 1, wherein the dose is delivered in a single pulse.

18. The computer system of claim 1, wherein the model is a function of oxygen pressure by incorporation a linear model of oxygen depletion in which $$p = p_0 - Rd$$

where the $p_0$ is the initial partial oxygen pressure and is expressed in terms of $[pO_2 \text{ mmHg}]$, d is the dose in Gy and the depletion rate R is expressed in terms of $[pO_2 \text{ mmHg/Gy}]$.

19. The computer system of claim 18, wherein the linear model of oxygen depletion is approximated by a histogram.

20. A radiation treatment system comprising the computer system of claim 1;

a radiation system for applying a radiation treatment; and a control system for controlling the radiation system wherein the computer system is configured to control the radiation system by outputting parameters to be implemented by the radiation system.

21. A computer-implemented method for analysing a radiation treatment plan using a dose of flash radiation to irradiate a volume within a patient, the method comprising obtaining oxygen pressure information for the volume to be irradiated;

obtaining parameters from a patient treatment plan;

inputting the obtained oxygen pressure information and parameters in to a model which predicts complex damage within the irradiated volume caused by the dose of flash radiation;

outputting a prediction, using the model, of the complex damage caused within the volume by the dose of flash radiation; and quantifying, using the prediction, a level of damage to healthy tissue within the irradiated volume;

wherein complex damage is damage which is more complex than a double strand break within DNA in patient tissue and wherein the model is a function of energy of particles within the radiation and oxygen pressure which varies with time.

22. A method of deriving a radiation treatment plan comprising analysing a radiation treatment plan using the method of claim 21, adjusting at least one of the parameters obtained from the patient treatment plan and outputting the at least one adjusted parameters.

23. A non-transitory data carrier carrying code which, when implemented on a processor, causes the processor to carry out the method of claim 22.

* * * * *